United States Patent [19]
Russell et al.

[11] Patent Number: 5,922,976
[45] Date of Patent: Jul. 13, 1999

[54] METHOD OF MEASURING AEROSOL PARTICLES USING AUTOMATED MOBILITY-CLASSIFIED AEROSOL DETECTOR

[75] Inventors: Lynn M. Russell, Boulder, Colo.; Richard C. Flagan, La Canada; Shouhua Zhang, Arcadia, both of Calif.

[73] Assignee: California Institute of Technology, Pasadena, Calif.

[21] Appl. No.: 08/730,037

[22] Filed: Oct. 11, 1996

Related U.S. Application Data

[60] Provisional application No. 60/005,098, Oct. 12, 1995.

[51] Int. Cl.$^6$ .................................................. G01N 15/02
[52] U.S. Cl. .......................................................... 73/865.5
[58] Field of Search ........................... 73/865.5; 364/555; 356/37, 335; 324/71.4; 702/128

[56] References Cited

U.S. PATENT DOCUMENTS

| | | | |
|---|---|---|---|
| 3,526,828 | 9/1970 | Whitby | 324/71.4 X |
| 3,763,428 | 10/1973 | Preist | 73/865.5 X |
| 4,633,714 | 1/1987 | Mazumder et al. | 73/865.5 X |
| 4,761,074 | 8/1988 | Kohsuka et al. | 356/336 X |
| 5,150,036 | 9/1992 | Pourprix | 73/28.02 X |
| 5,247,842 | 9/1993 | Kaufman et al. | 73/865.5 |
| 5,507,847 | 4/1996 | George et al. | 55/486 |
| 5,606,112 | 2/1997 | Flagan et al. | 73/28.04 |
| 5,621,208 | 4/1997 | Pourprix | 250/287 |

FOREIGN PATENT DOCUMENTS

| | | | |
|---|---|---|---|
| 1463953 | 12/1966 | France | 73/865.5 |
| 3413426 | 10/1985 | Germany | 73/865.5 |
| 545900 | 2/1977 | U.S.S.R. | 73/865.5 |

OTHER PUBLICATIONS

Patent Abstracts of Japan Grp P1130, vol. 14, No. 516 Abs pub date Nov. 13, 1990 (02–216027) "Manufacture of Reference Body for Calibration of Surface Pollution Detector".

Patent Abstracts of Europe (DE 04313238 A1) Oct. 27, 1994 "Method and apparatus for fractionating measurement of aerosols".

Patent Abstracts of Europe (WO 09606341 A2) Feb. 29, 1996 "Aerosol Particle Grading Process" Andreas Schmidt–Ott et al.

Patent Abstracts of Japan (08–261911) Oct. 11, 1996 "Particle Size Distribution Measuring Device" Yasuo Kosake et al.

Adachi, et al., Facilitated aerosol sizing using the differential mobility analyzer, Aer. Sci. Tech., 12: 1990. pp. 225–239 month not given.

Crump, et al., Turbulent deposition and gravitational sedimentation of an aerosol in a vessel of arbitrary shape., J. Aerosol Sci., 12: 1981. No. 14, pp. 405–415 month not given.

Daum and Springston, Trophospheric sampling with aircraft, Measurement Challenged in Atmospheric Chemistry, pp. 101–132, 1993. Month not given.

Frick, et al., Airship measurements of aerosol size distributions, cloud droplet spectra, and trace gas concentrations in the marine boundary layer, Bull Am. Met. Soc., 74: No. 11 Nov. 1993, pp. 2195–2202.

Hagen and Alofs, Linear inversion method to obtain aerosol size distributions from measurements with a differential mobility analyzer, Aer. Sci., 2: 1983. pp. 465–475, month not given.

(List continued on next page.)

Primary Examiner—Thomas P. Noland
Attorney, Agent, or Firm—Fish & Richardson P.C.

[57] ABSTRACT

An aerosol detection system for measuring particle number distribution with respect to particle dimension in an aerosol sample. The system includes an alternating dual-bag sampler, a radially classified differential mobility analyzer, and a condensation nucleus counter. Pressure variations in sampling are compensated by feedback control of volumetric flow rates.

6 Claims, 12 Drawing Sheets

OTHER PUBLICATIONS

Hegg, et al., Aerosol size distributions in the cloudy atmospheric boundary layer of the North Atlantic Ocean, J. Geophys. Res., 98: No. 5, pp. 8841–8846, May 20, 1993.

Hoppel, W.A., Determination of the aerosol size distribution from the mobility distribution of the charged fraction of aerosols, J. Aerosol Sci., 9: 1978., pp. 44–54 month not given.

Hudson and Clarke, Aerosol and cloud condensation nuclei measurements in the Kuwait plume, J. Geophys. Res., 97:, No. D13, pp. 14533–14536, Sep. 20, 1992.

King, et al., Optical properties of marinr stratocumulus clouds modified by ships, J. Geophys Res., 98:, No. D2, pp. 2725–2735, Feb. 20, 1993.

Knutson and Whitby, Accurete Measurement of Aerosol Electric Mobility Moments, J. Aerosl. Sci., 6:, 1975, pp. 453–460, month not given.

McMurry and Rader, Aerosol wall losses in electrically--charged chambers, Aer. Sci. Tech., 4:249–268, 1985.

Okuyama, et al., Turbulent coagulation of aerosols in a stirred tank, J. Chem. Eng. Jpn., 10:142–147, 1977. No. 2.

Quant, et al., Performance of condensation particle counters with three continous–flow designs, J. Aerosol. Sci., 23: 1992., Suppl. 1, pp. 5405–5408, month not given.

Russell, et al., Asymmetric instrument response resulting from mixing effects in accelerated DMA–CPC measurements, Aer. Sci. Tech., in press, 23: pp. 491–509, 1995. month not given.

Scheibel, et al., Generation of Monodisperse Ag–aerosol and NaCl–aerosol with particle diameters between 2–nm and 300–nm, J. Aerosol Sci., 14: 1983., No. 2, pp. 113–126 month not given.

Stolzenberg, et al. An ultra fine aerosol condensation nucleus counter, Aer. Science Tech., 14: pp. 48–65 1991 month not given.

Wang, et al., Scanning electrical mobility spectrometer, Aer. Sci. Tech., 13: 1990. pp. 230–240 month not given.

Wiedensohler, A., An approximation of the bipolar charge--distribution for particles in the sub–micron size range, J. Aerosol Sci., 19: 1988. pp. 387–389 month not given No. 3.

Winklmayr, et al., A new electromobility spectrometer for the measurement of aerosol size distributions in the size range from 1 to 1000 nm, J. Aerosol Sci., 28: 1991., No. 3, pp. 289–296 month not given.

Zhang et al., Radial differential mobility analyzer, Aer. Sci. Tech., in press, 1995. month not given pp. 357–372.

METHOD OF MEASURING AEROSOL PARTICLES USING AUTOMATED MOBILITY-CLASSIFIED AEROSOL DETECTOR

This application claims the benefit of U.S. Provisional Application No. 60/005,098, filed on Oct. 12, 1995.

FIELD OF THE INVENTION

The present invention relates to aerosol measurements and technology. More particularly, the present disclosure describes a precision aerosol detection system for fast characterization of fine particle size distributions in a pressure-changing environment.

BACKGROUND AND SUMMARY OF THE INVENTION

Aerosol measurements characterize the size, concentration and composition of particles suspended in the atmosphere. Measuring the particle size distribution provides the concentration of particles as a function of size. Atmospheric particles influence climate change, radiative transfer, visibility, and air quality. Measurements of the concentration and sizes of particles present in the atmosphere allow quantification of pollutant effects and monitoring particulate growth.

Aerosol instruments can be used for carrying out high-resolution, in-situ aerosol measurements from aircraft and ships. These measurements can probe the spatial and temporal variability of the tropospheric aerosol. A striking example of the effect of spatial variability of aerosol characteristics on cloud properties is provided by ship tracks, first observed from satellites, and later from aircraft measurements. Ship tracks provide a dramatic example of the ability of aerosols to alter the resulting cloud characteristics; measuring this microphysical evolution by means of in-situ measurements was an important goal of the Monterey Area Ship Track (MAST) Experiment. These spatially well-defined perturbations of the aerosol concentration and composition and of cloud properties provide an opportunity to study the broader question of the impact of anthropogenic emissions on cloud properties.

Theoretical studies have predicted that both marine and anthropogenically-influenced tropospheric aerosols should vary diurnally as a result of photochemical reactions resulting in secondary new particle formation and aerosol growth. Such work suggests that the aerosol size distribution will evolve during the day through a series of characteristic size distributions indicative of periods of nucleation and condensation. Providing in-situ evidence for such direct dependence of aerosol properties on other atmospheric variables suggests studies of marine boundary layer and free tropospheric aerosol with aircraft instrumented to measure size distributions quickly and automatically.

Airborne measurements of submicron aerosol size distributions at a frequency capable of resolving the differences, for example, between the cloud line features and surrounding clouds are desirable in order to characterize small-scale or ephemeral features in the atmospheric aerosol. Many of the commercially-available submicron aerosol classification and counter designs are not suited for this application partially because of the long sampling times required to characterize the submicron size distribution extending over two or more decades in particle diameter.

One type of the prior-art airborne aerosol instruments use optical particle counters aboard the aircraft. These instruments provide valuable insight into the variation of aerosol with altitude, and the character of aerosol in and above the clouds. One such system was described by Radke et al. for obtaining size distribution information with an optical particle counter (OPC) for particles greater than 0.1 mm diameter in "Direct and remote sensing observations of the effects of ships on clouds", Science, Vol. 246, pp. 1146–1149, 1989. Clarke et al. introduced the Thermo-Optical Aerosol Detector (TOAD) to characterize both the dry aerosol distribution and its volatility in 1991 ("A thermo-optic technique for in-situ analysis of size-resolved aerosol physicochemistry", Atmos. Env., Vol. 25A, pp. 635–644). Hegg et al. and Clarke extended the effective size range of aerosol measurement using mobility-classification to below 20 nm diameter. Detailed descriptions of their work can be found in "Aerosol size distributions in the cloudy atmospheric boundary layer of the North Atlantic Ocean", J. Geophys. Res., Vol. 98, pp. 8841–8846, 1993 and "Airborne measurements of aerosol properties in clean and polluted air masses during ASTEX", EOS Proceedings of the 1993 AGU Spring Meeting, Apr. 20 of 1993.

Several constraints are inherent to aircraft-based submicron aerosol measurement, including limitations on size, weight, and power as well as the necessity for making fast measurements while adjusting rapidly for changing pressure, temperature, and humidity conditions. The need for rapid measurements derives from the aircraft's speed relative to the spatial scale of changes in aerosol properties. The spatial resolution possible with an airborne instrument is determined both by the speed of the instrument and the speed of the aircraft. Conventional differential mobility analysis requires a sampling period of about 10 min. If continuous sampling methods were employed, the resulting size distribution would represent, for example, at a speed of 100 m/s, a composite distribution of sized aerosol concentrations for a 60-km flight leg. Since air mass characteristics can change drastically over 60 km, several prior-art systems employed a grab sampling approach in which air is drawn into a holding chamber and stored while a single measurement is processed. Radke et al. employed a 90 l steel cylindrical chamber with a floating piston filled by ram pressure to store the aerosol for size classification, and were thus able to store a sample collected in 5 seconds (see, the above referenced publication in 1989). Hegg et al. also employed a large (about 2.5 $m^3$) polyethylene bag for analysis over a ten minute period of size classification (see, the above referenced publication in 1993).

The approach of grab sampling has successfully provided in-flight snapshots of aerosol in air masses, which have been coupled with continuous condensation nuclei (CN) measurements to determine the aerosol's spatial variability. Measurement speed still limits both the frequency with which complete distributions can be acquired and the instrument's lower detection limit. Diffusional deposition of aerosol particles on the walls of a sampling vessel can reduce the number concentrations dramatically for long counting times. Consequently, the chamber's volume must be chosen such that particle losses during sampling and analysis are minimized. Particle losses in a chamber are also exacerbated by electrostatic enhancement of charged particles on the chamber walls. Hegg et al. measured ultra fine particles during a 10-min. sample measurement protocol by employing a 2.5-$m^3$ chamber.

To size particles smaller than 0.1 $\mu m$ in diameter, a differential mobility analysis is usually employed. This technique is described in detail by Knutson and Whitby, in "aerosol classification by electrical mobility" in J. Aerosol Sci., vol. 6, p. 453, 1975. A differential mobility analyzer separates charged particles according to their migration velocities in an applied electric field. Differential mobility analysis is accomplished by introducing a small aerosol flow near one electrode of a two-electrode apparatus, with a larger particle-free sheath flow separating that aerosol from the second electrode. An electrical potential drives particles of appropriate polarity across the sheath flow toward the opposite electrode. At a location downstream from the aerosol inlet, small classified aerosol sample flow is extracted, which the remaining flow is discharged to an exhaust. Only particles that migrate within a narrow range of velocities are included in the classified aerosol sample flow. Particles with higher migration velocities deposit on the counter electrode while those with lower migration velocities are discharged with the exhaust flow. In measurements of differential mobility size distribution, the classified aerosol particles are transported to a detector for counting. Because the particles of interest are too small to be efficiently detected optically, they are commonly grown by vapor condensation in a detector known as a condensation nucleus counter.

The particle size is inferred from the migration velocity based on the relationship between particle size and the electrical mobility of the particles. This is described by Flagan and Seinfeld in "Fundamentals of Air Pollution Engineering", Prentice-Hall, 1988. The electrical mobility, Z, is defined as the ratio of the migration velocity $U_m$ to the strength of the applied electrical field, E, $$Z = \frac{v_m}{E}. \qquad (1)$$

For spherical particles carrying V electrical charges, the mobility Z can be written as $$Z = \frac{ve}{3\pi\mu D_p} C_c\left(2\frac{\lambda}{D_p}\right), \qquad (2)$$

where $\mu$ is the gas viscosity, $D_p$ is the particle diameter, $C_c$ is an empirically-determined slip correction factor that accounts for noncontinuous aerodynamic effects that become important where the particle diameter is comparable to or smaller than the mean-free-path $\lambda$ of the gas molecules, and e is the elementary unit of change. A commonly employed form for this slip correction factor is $$C_c = 1 + Kn\left(1.257 + 0.4\exp\left(-\frac{0.11}{Kn}\right)\right), \qquad (3)$$

where $$Kn = \frac{2\lambda}{D_p} \qquad (4)$$

is the Knudsen number. Under typical operating conditions, only a fraction of the particles are charged, and a majority of those charged particles carry one charge, i.e., V=1. Most mobility classifications are performed with positively charged particles.

The migration velocity required for a particle to be transmitted from the aerosol inlet flow to the classified aerosol outlet flow of the differential mobility analyzers depends on the geometry of the classifier and on the four flow rates, i.e., an input sample flow rate, an input sheath flow rate, an output sample flow rate, and an output excess flow rate. The size of the particles to be classified is selected by adjusting the voltage such that particles with the mobility of particles of the desired size will migrate at the velocity required for transmission. The size distribution of the aerosol is determined by making measurements of the concentrations at a number of sizes spanning the size range of interest.

Differential mobility analysis has traditionally been performed by making a sequence of measurements at different electric field strengths, i.e., at different voltages applied across the two electrodes of the classifier. Although this method is effective, it is slow, requiring times ranging from several minutes to more than an hour to measure a size distribution depending on the size range that is probed and the resolution that is sought. Wang and Flagan accelerated the measurements dramatically by exponentially ramping the voltage and counting the particles continuously, thereby eliminating the delays between successive measurements that are needed to ensure representative data at each mobility with the stepping-mode of differential mobility analysis. A complete size distribution can be measured in less than one minute with this accelerated scanning-mode of differential mobility analysis. Wang and Flagan disclosed this in "Scanning electrical mobility spectrometer" in Aerosol Sci. Technol., 13, pp. 230–240, 1990.

The speed with which aerosol size distributions may be characterized is limited by the time required to obtain significant particle counts for each size channel, which, for a given ambient concentration, is a function of the counting statistics and efficiency of the detector and the flow profile in the measurement system. In single-particle counting operation, the counting statistics of condensation nucleus counters (CNCs) are governed by the number of particles that can be counted in a specified time interval. For a stream of air containing $N_i$ particles ($cm^{-3}$) with flow rate $Q_s$ at the detector, and detection efficiency s($D_p$, V) for fraction p($D_p$, V) of particles of diameter $D_p$ carrying V charges, the measured signal $S_i$ for channel i is proportional to the product, $N_iQ_s$ s($D_p$, V s($D_p$, V).

Among the commercially available counters, the TSI 3025 condensation nucleus counter has one of the highest detection efficiency for ultra fine (less than 10-nm diameter) particles. However, in order to obtain uniform saturation the sample flow is surrounded by a sheath flow that dilutes the flow to the counter of 0.3 liter per minute by a factor of 10, so that $Q_s$ is 0.03 liter per minute. This was described by Stolzenburg and McMurry in "An ultrafine aerosol condensation nucleus counter" in Aerosol Sci. Technol., Vol. 14, pp. 48–65, 1991. Other condensation nucleus counters, in particular TSI models 3010 and 3022, have detector flow rates of 1 liter per minute, but have 50% detection efficiency cutoffs of 10 nm and 8 nm, respectively, such that size distributions may not be extended to the ultra fine range.

Airborne measurements of particle size distributions by differential mobility analysis are further complicated by pressure variations that accompany altitude changes. Mobility classification requires precise control of several coupled flow rates. Continuous measurements require immediate and accurate adjustment of those flows in response to changes caused by pressure variations. As discussed previously, the above-mentioned prior-art systems and methods for airborne particulate growth are manual-intensive, spatially and temporally resolution-limited. In addition, the signal to noise ratios in clean air are low.

The present invention discloses components and a system design for aerosol measurements with significantly improved spatial and temporal resolution, automated flow control, and high counting efficiency at particle sizes less than 0.5 mm. A preferred embodiment, the Automated Mobility-Classified-Aerosol Detector (AMCAD), has an alternating dual-bag sampler, a particle charger, an improved differential mobility analyzer (DMA), and a condensation nucleus counter (CNC). The implementation of automated feed back control of flow rates allows the preferred embodiment of the present invention to achieve high-resolution and high precision measurements under changing pressures. The AMCAD also controls the temperatures of the saturator and the condenser in the condensation nucleus counter to achieve consistent high counting efficiency as the temperature of the incoming aerosol sample changes. The adverse effects associated with the humidity level of the aerosol sample are reduced by desiccating the dilution flow that mixes with the aerosol sample flow at the entrance of the condensation nucleus counter.

The advantages, sophistication, and significance of the present invention will be more apparent in light of the following detailed description of the preferred embodiment thereof, as illustrated in the accompanying drawings.

DESCRIPTION OF THE PREFERRED EMBODIMENT

Figure 1:
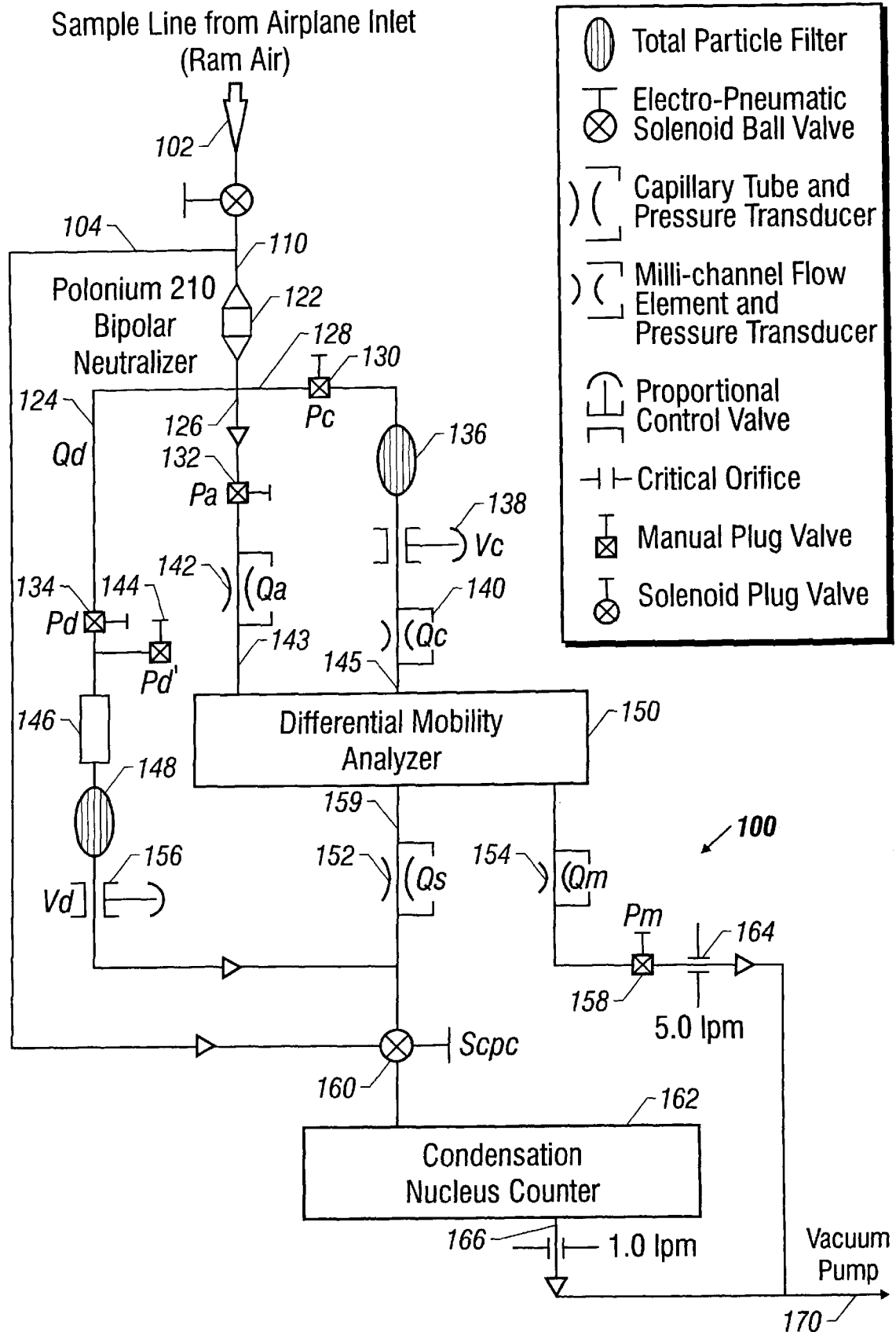
FIG. 1 is a schematic of the preferred embodiment of the radially classified aerosol detector (AMCAD) of the present invention.

The present invention discloses an automated mobility-classified aerosol detector (AMCAD) 100 for unattended, high-resolution airborne measurement of particle size distributions of atmospheric aerosols. FIG. 1 is the schematic of the preferred embodiment. The principal components include an aerosol charger-neutralizer 122, a differential mobility analyzer (DMA) 150, an ultra fine condensation nucleus counter (CNC) 162 and various flow control components.

System Design of Radially-Classified Aerosol Detector

A sample input line 102 connecting to the air inlet of the aircraft is divided into two channels, a bypass channel 104 for unclassified and direct aerosol particle density measurements which goes to the input port 161 of the CNC 162 and a sampling channel 106.

A ball-valve 120 controls the sampled aerosol flow to the aerosol charger-neutralizer 122. The particles in the sampled aerosol are charged in the charger neutralizer 122 and the aerosol flow is split into three channels. A first aerosol flow, the dilution flow $Q_d$, goes into channel 124 and is desiccated by a desiccator 146 therein. A total particle filter 148 operates to filter out the particles in the desiccated dilution flow. The desiccated clean air flow in the dilution flow containing a minimal amount of particles is then routed to mix with the aerosol sample flow at the output port 159 of the DMA 150. A second aerosol flow goes to the sampling channel 126 that feeds aerosol particles to the sampling input port 143 of the DMA 150. The aerosol flow rate $Q_a$ in the sampling channel 126 is measured by a flow meter 142 having a capillary tube and pressure transducer therein. A third aerosol flow to channel 128 is filtered by a total particle filter 136. The filtered clean sheath flow is routed to the air input port 145 of the DMA 150. A flow meter 140 having a milli-channel flow element and a pressure transducer measures the flow rate $Q_c$ of the clean sheath flow.

The DMA 150 operates to sample the aerosol flow from the input port 143 and generates a sample flow at the sample output port 159 and a main excess flow at the output port 157. The sample flow rate $Q_s$ is measured with a flow meter 152. The sample flow is further mixed with the desiccated clean air flow from the channel 124 to reduce the moisture in the sample flow. The CNC 162 subsequently measures the number of particles in the sample flow. The main excess flow has the unsampled aerosol particles from the DMA 150. Its flow rate $Q_m$ is controlled by an critical orifice 164 and monitored by a flow meter 154. The output of the system 100 is dumped to a vacuum pump 170.

Dual-Bag Sampler

Figure 2:
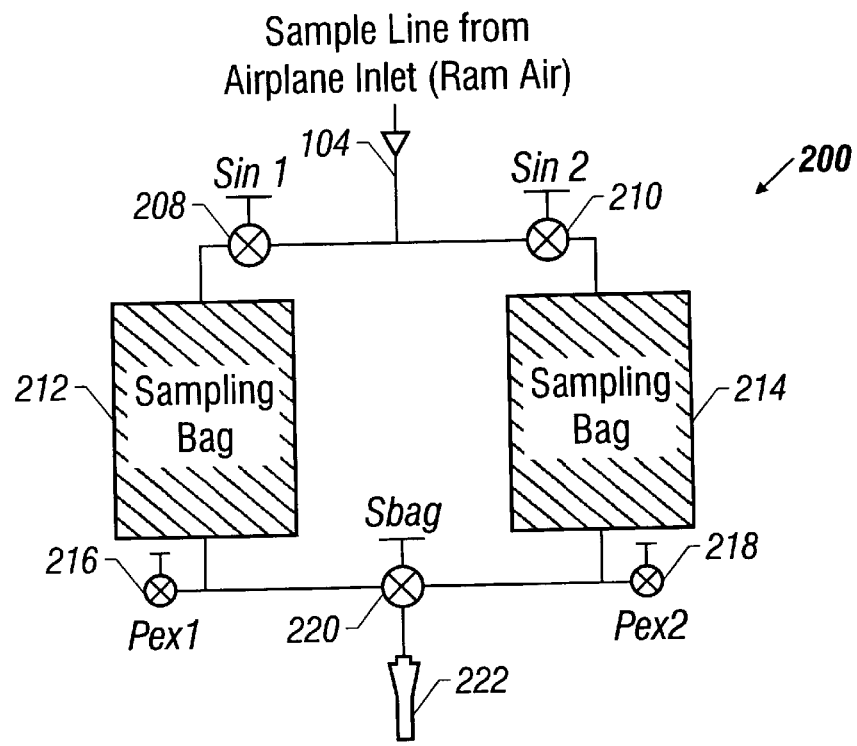
FIG. 2 depicts a preferred embodiment of the dual-bag sampler.

A sampling device can be inserted at the inlet 102 and the input port 110 of the aerosol detector 100 shown in FIG. 1. One preferred embodiment 200 is illustrated in FIG. 2. The sampler 200 includes two substantially identical sampling bags 212 and 214 that are disposed in parallel relative to each other in the flow system. Two ball-valves 208 and 210 are respectively connected at the input ports of the sampling bags 212 and 214 to regulate the direction of the aerosol flow in the sampler 200.

According to the preferred embodiment, the two sampling bags 212 and 214 of the sampler 200 are preferably used in an alternating way such that one bag is being flushed then filled, while the other bag is being used for measuring the collected aerosol. This is one of the factors in the present system 100 to increase the spatial resolution of a measurement flight track. The bags are preferably constructed from electrically conducting polymer materials such as carbon-impregnated polyethylene. Each of the two bags are mounted between two disk-like elements that are preferably steel-shim-covered Plexiglas. In one prototype sampler, the disks were about 12 inches in diameter and were separated by a distance of 12 inches, making the volume of each sampling bag to be about 1356 cubic inch.

A rigid frame (e.g., made of aluminum metal) provides a housing for the two sampling bags and other parts. The frame is preferably designed to mount in a standard 19" rack. The air enters the aircraft through a tubing with a preferable inner diameter near 2 cm. The material for the tubing is preferred to be an electrically conducting plastic material such as carbon-impregnated polyethylene. The regulating valves 208 and 210 are preferably ball valves operated by an electropneumatic solenoid system. In operation, the bag sampler 200 captures a fixed volume of air from which the aerosol is drawn into the classifier DMA 150 and the detector CNC 162. After filling a bag, the flow is extracted at a fixed flow rate (e.g., approximately 6 liter per minute) through the charger-neutralizer 122 in which the aerosol attains a steady-state bipolar charge distribution.

Improved Bipolar Neutralizer

Figure 3:
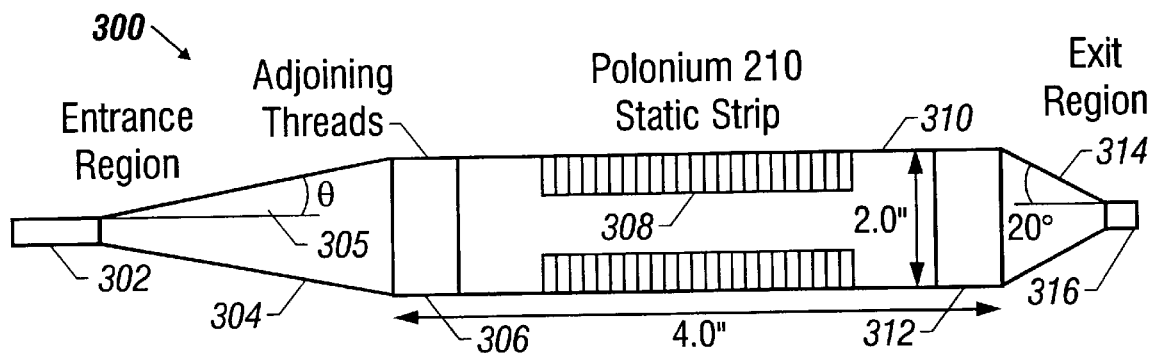
FIG. 3 shows the design of the housing for a bipolar charger.
Figure 4:
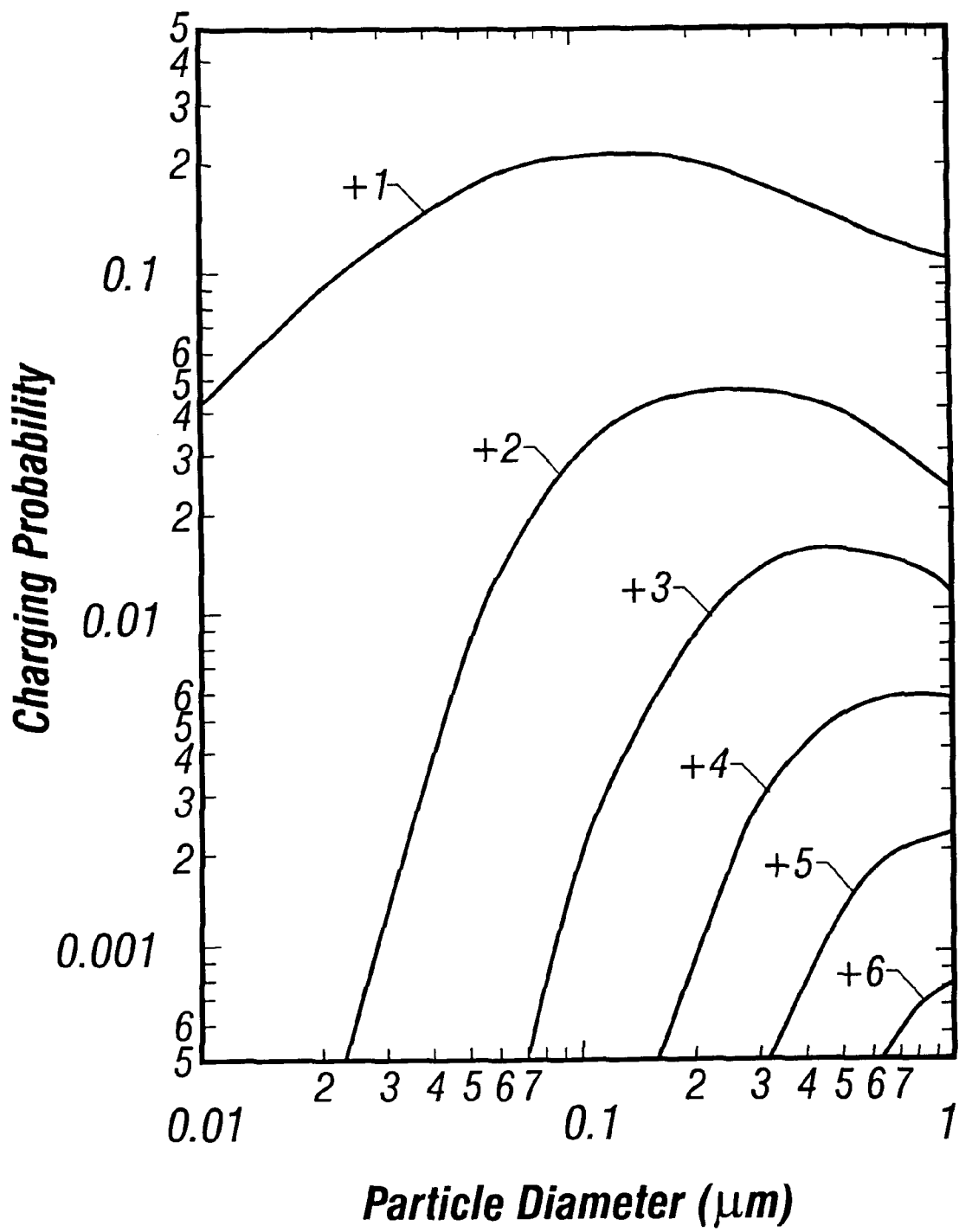
FIG. 4 shows the particle charging efficiency in the bipolar neutralizer based on calculations by Fuchs (1963) and Wiedensohler (1988).

The charger-neutralizer 122 in accordance with the present invention is preferably a bipolar neutralizer having a plurality of Polonium 210 static strips (e.g., four strips). This device 122 produces electrical charges on the aerosol sample from the sampler 200. The inventors of the present invention designed a special charger housing 300 for the charger-neutralizer 122 as illustrated in FIG. 3. The housing 300 operates to maximize uniform exposure to the Polonium alpha particle emissions while minimizing the dead time and mixing. The aerosol flow from the sampler 200 enters the housing 300 at an inlet 302 which connects to the entrance region 304. The main chamber 310 has Polonium 210 static strips that emits alpha ("α") particles. The α particles impact the gas molecules, leading to electron emission and producing positive ions. A sequence of charge exchange reactions produces additional gas ions. The gas ions transfer electrical charges to the aerosol particles. The charged aerosol flow goes through the exit region 314 to exit at an output port 316. The angle q at the neutralizer entrance is designed to prevent recirculation of streamlines in the entrance region 305. The angle q is preferably set at about 7 degrees. The neutralizer 122 was designed to attain an equilibrium charge distribution for residence times corresponding to flow rates of up to 15 liter per minute. The charge distribution $p(D_p, V)$ resulting by diffusion charging of particles by collision with ions produced by α particles is described by Wiedensohler in "An approximation of the bipolar charge-distribution for particles in the sub-micron size range", J. Aerosol Sci., Vol. 19, pp. 387–389, 1988. This is shown in FIG. 4. The charging probability has been checked experimentally by D. Covert and was found to be within the experimental uncertainty of the theoretically expected value for steady-state charging of an aerosol.

Modified Radial Differential Mobility Analyzer

The classifier DMA 150 samples charged particles according to their size based on the mobility of the particles in an electrical field. Though many DMAs can be used with the preferred system AMCAD 100 of FIG. 1, the preferred embodiment 100 preferably uses a modified radially classified differential mobility analyzer (RDMA) that was originally developed at the California Institute of Technology. A detailed description of the RDMA can be found in S. H. Zhang et al., "Radial differential mobility analyzer", Aerosol. Sci. Technol., vol. 23, pp. 357–372, 1995, which is incorporated herewith by reference. The RDMA has many advantages over other differential mobility analyzers including reduced particle losses at the aerosol inlet, a short residence time (one-fifth that of the most common commercial DMAs), and more compact design and light weight. The RDMA thus has smaller diffusion losses and reduced broadening for small particles. The modified RDMA used in the AMCAD system 100 has inner dimensions substantially identical to those described by Zhang et al. in the above referenced literature, with a disk separation of 1.00 cm, an entrance radius of 5.09 cm and an exit radius of 0.25 cm. The inventors of the present invention minimized the weight of the modified RDMA by thinning the outer dimensions. The electrically conducting parts can be made of a conducting material including metals such as aluminum and stainless steel. The spacer can be made of an insulating material including a plastic material such as Delrin® or ceramic. The resulting classifier weighs about 4 kg and has a dimension of 5 cm in thickness and 20 cm in diameter. In the system shown in FIG. 1, the RDMA is fastened to vertical struts and rests on a notched and rubber-lined aluminum support. The absolute pressure is monitored in the RDMA with a pressure transducer mounted at the excess flow exit 157, and the relative humidity and temperature are measured with probes downstream.

The inventors of the present invention further designed an analog exponential ramp circuit (ERC) to significantly enhance the measurement precision of the RDMA, specially at the fine particle end of the size spectrum. Rapid mobility measurements are made by classifying particles in an electric field that varies exponentially with time according to Wang and Flagan in "Scanning electrical mobility spectrometer" in Aerosol Sci. Technol., 13, pp. 230–240, 1990. In both the original implementations of this method and its recent commercial version (TSI Scanning Mobility Particle Sizer), the high voltage was controlled using a high-resolution (16 bit) digital-to-analog converter. Although this approach produces a smooth exponential ramp at high voltages, the discrete voltage steps become appreciable at low voltages, introducing uncertainty at the fine particle end of the size spectrum. Use of higher resolution D/A converters (e.g., 18 bit to 22 bit) can extend the useful range of a digitally controlled voltage ramp.

The analog exponential ramp circuit (ERC) 500 in accordance with the present invention is illustrated in FIG. 5. The ERC 500 provides an analog signal from 0 to 5 volts at the output 520. This circuit 500 is used to drive one or more high voltage power supplies (e.g., Bertan, model 602C-100N:CS2562) to produce an voltage output in a range from about 3 volts to about 10000 volts, thereby providing accurate voltage control over four decades. The ERC 500 includes the following parts: (1) an integrator 505 having an operational amplifier 501, a capacitor 504, and a resistor 506; (2) an inverter/follower 507 having an operational amplifier 502, two resistors and a solid-state analog switch 514; and (3) a logic control circuit having a comparator 510, a solid-state analog switch 516, and a TTL circuit 512.

The output voltage at the output 520 of the ERC 500 is given by the following relation:

$$V = V_0 \exp\left(\pm \frac{t}{\tau_r}\right), \tag{5}$$

where the amplitude $V_0$ is given by $$V_0 = V_{min}, \text{ for increasing scan,} \tag{6}$$

and the characteristic time for the voltage ramp $\tau_r$ is $V_0=V_{max}$, for decreasing scan, (7)

determined by $$\tau_r \equiv \frac{RC}{\alpha}, \quad (8)$$

in which a is the potentiometer ratio in the circuit 500 and provides a coarse adjustment of $\tau_r$. The capacitance C of the capacitor 504 is fixed. The characteristic time $\tau_r$ can also be varied by tuning resistance R of the resistor 506, which includes a 10-turn potentiometer 508. The ERC ramp is initiated by a TTL low pulse with the TTL controller 512. The solid-state analog switch 516 feeds the predetermined upper voltage limit $V_{max}$ to the comparator 510 when the ERC 500 is in an up-scan process, or the lower voltage limit $V_{min}$ when the ERC 500 is in a down-scan process. When the ERC 500 is in an up-scan and the ramping voltage at the output 520 reaches $V_{max}$, the comparator 510 sends a signal to the TTL circuit 512 to switch the analog switch 514 from the ground point 517 to the point 518, thus converting the operational amplifier 502 from an inverter to a follower. This operation makes the analog switch 516 to feed the comparator 510 with a lower voltage limit. The ERC 500 is ready for a down-scan. When the ERC 500 is in a down-scan and the ramping voltage at 520 reaches $V_{min}$, the comparator 510 sends a signal to the TTL circuit 512 to convert the operational amplifier 502 to an inverter by switching the switch 514 from the point 518 to the ground point 517. Meanwhile, the analog switch 516 is changed to feed the comparator 510 with an upper voltage limit, $V_{max}$. Thus, the ERC 500 is ready for an up-scan.

Figure 6:
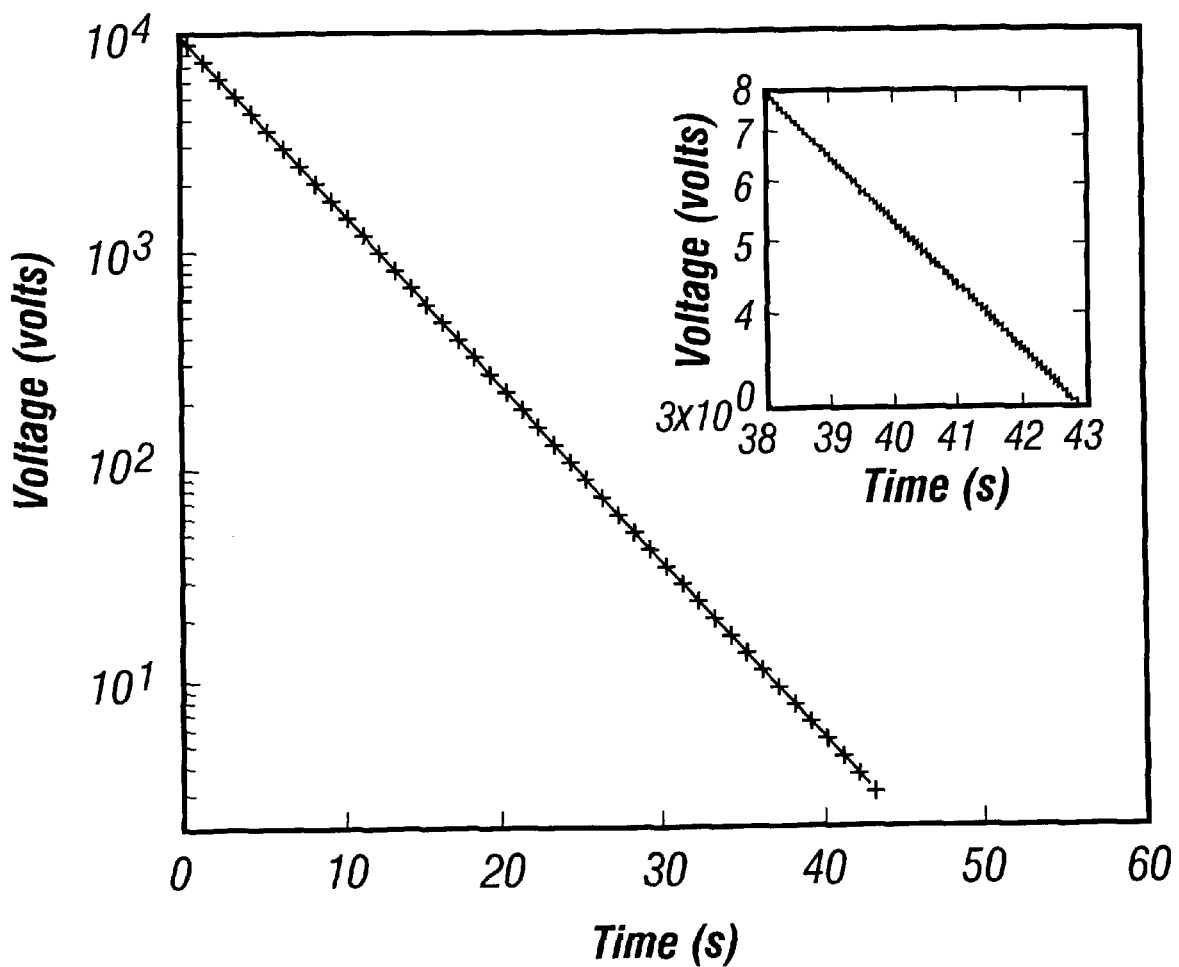
FIG. 6 shows both calculated voltage response and measured voltage response versus time of the exponential ramp circuit shown in FIG. 5.

FIG. 6 shows the measured output of the ERC 500. The crosses represent the data and the solid line represents the functions by Equations (5) and (8) for $\tau_r=5.35$ s, $V_{min}=3$ V, and $V_{max}=9490$ V. The insert illustrates high-resolution data at 100 Hz at low voltages.

Figure 5:
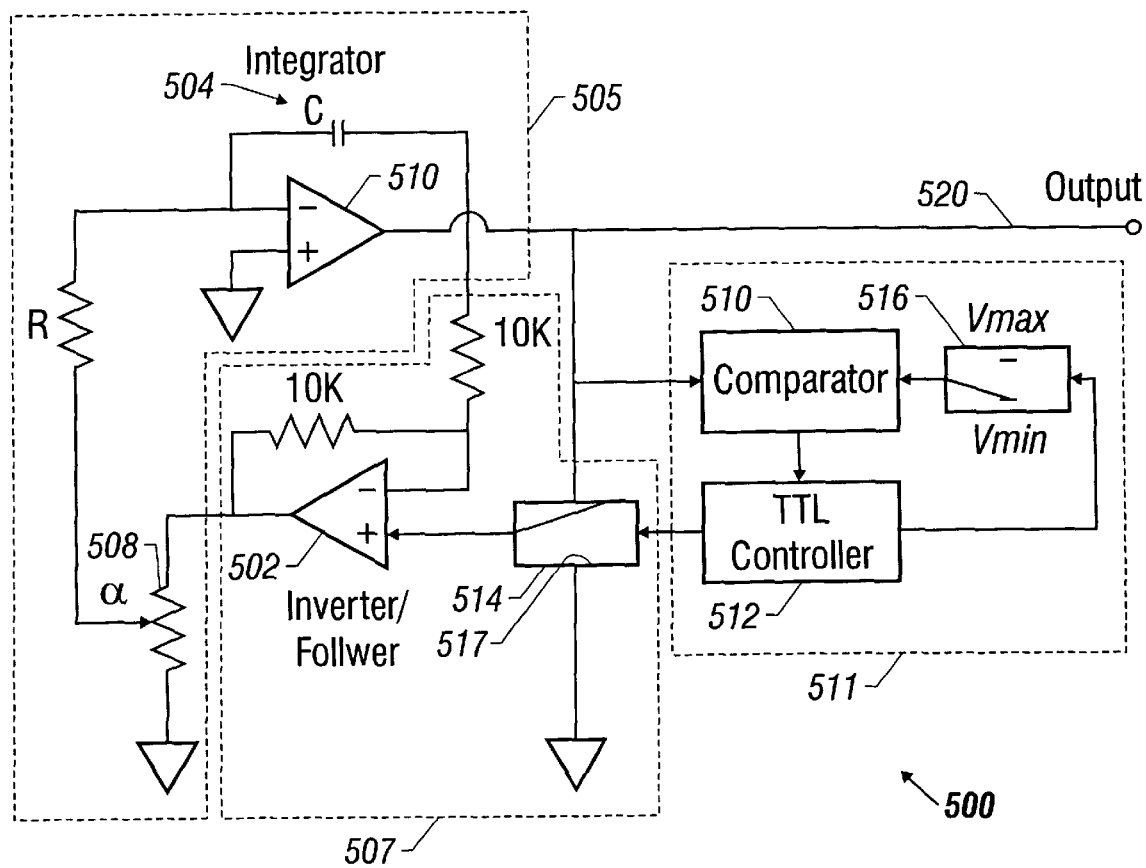
FIG. 5 shows the exponential ramp circuit in a functional block diagram.

Resolution of the particle classification possible with the RDMA is presented the above incorporated reference by Zhang et al. For the flow rates used here the diffusion loss data from Zhang et al. in "Radial differential mobility analyzer", Aerosol. Sci. Technol., Vol. 23, pp. 357–372 in 1995 may be interpolated to provide the estimate of expected diffusion losses of particles in the RDMA at the flow rates used for this configuration. The transfer function for the RDMA has the same functional form as that for the cylindrical DMA, although the geometric factors differ for the two instruments. The selection of particle size is controlled by the voltage applied to the RDMA, which is controlled by the ERC 500 of FIG. 5.

The RDMA 150 effectively eliminates most of the signal degradation associated with diffusion broadening in conventional electrostatic classifiers. The RDMA has an aerosol inlet 143 with minimal particle losses and a residence time one-fifth that of a commonly used commercial cylindrical DMA from TSI of St. Paul, Minn. (model 3071), leading to reduced diffusion losses and broadening for small particles. In addition, as shown in Table 1, the RDMA is more compact and lighter weight than its cylindrical counterparts, thus facilitating its use aboard aircraft.

TABLE 1

Dimensions of six differential mobility analyzer (DMA) designs

| Geometry | Group | Reference | Diameter Range[a] | Dimensions[b] (H x D) |
|---|---|---|---|---|
| Cylindrical-"long" | TSI, Inc. | Knutson and Whitby (1975) | 0.020–1.000 μm | 44 cm x 3.9 cm |
| | NRL | Hoppel (1978) | 0.010–1.2 μm | 86 cm x 10 cm |
| | Hauke | Winklmayr et al. (1991) | 0.010–1.000 μm | 60 cm x 6.6 cm |
| Cylindrical-"short" | TSI, Inc. | Adachi et al. (1990) | 0.002–0.001 μm | 10 cm x 3.9 cm |
| | Hauke | Winklmayr et al. (1991) | 0.001[c]–0.150 μm | 11 cm x 6.6 cm |
| | ISPN | Fissan et al. (1994) | 0.007–1.000 μm | 0.4 cm x 13 cm |
| Radial | CIT | Zhang et al. (1995) | 0.003[d]–0.500 μm | 1.0 cm x 10 cm |

[a]Unless otherwise noted, the lower bound is the 50% cutoff in transmission efficiency.
[b]Dimensions given are outer dimensions of flow volume. In each case the height (H) and diameter (D) are given.
[c]Transmission efficiencies were not measured. Lower bound is range specified in paper.
[d]Transmission efficiency measured at this diameter is 92%. No data are available for smaller sizes.

High-Counting-Efficiency Condensation Nucleus Counter

The inventors recognized limitations of the existing condensation nucleus counters and modified a commercial CNC TSI-3010 to improve the device performance.

Condensation nucleus counters (CNCs) operate on the principle of growing aerosol particles from the fine or ultra fine size range to sizes that are large enough to be optically detected. The sample is first saturated with condensible vapor at an elevated temperature $T_s$ in the saturator in the CNC; the vapor is then condensed onto the particles by cooling the sample stream to $T_c$ in the condenser of the CNC. The supersaturation in the condenser, and hence the probability that particles of a given size will grow by condensation, are controlled primarily by the difference in the temperatures $T_s$ and $T_c$, as described by the following relation based on the Clausius-Clapeyron equation for liquid-gas equilibrium:

$$S \equiv \frac{P_c}{P_{sat}(T_c)} = \frac{P_{sat}(T_s)}{P_{sat}(T_c)} = \exp\left[\frac{\Delta H_v}{R}\left(\frac{1}{T_c} - \frac{1}{T_s}\right)\right], \quad (9)$$

where $DH_v$ is the liquid's latent heat of vaporization.

Scanning mobility measurements limit the time available for counting particles in any channel. Acquiring a statistically significant number of counts within the available counting time (e.g., 1 second) requires that particles be counted from a large sample flow rate. The commercial CNC TSI model 3010 Condensation Particle Counter provides an adequate flow rate (1 liter per minute), but its 50% detection cutoff is 12 nm in its standard configuration (Quant et al., 1992). The inventors of the present invention modified the commercial instrument to increase the temperature difference $DT=T_s-T_c$ from the nominal value of 17° C. This extends its detection limit to smaller sizes. The inventors found that this cutoff can be decreased to 8 nm by increasing DT to 25° C. By augmenting the heating capabilities in the saturator with a heating mat and the cooling capabilities in the condenser with an additional thermo-electric device (TED) placed adjacent to the original TED, the counting efficiency can be further enhanced. These modifications were implemented in a custom-built 3010 CPC (TSI). In the original TSI 3010 CPC, only the temperature difference, DT, is controlled. Specifying only DT can lead to drift in $T_s$ and $T_c$ as the operating conditions (e.g., cabin temperature) shift. Since the supersaturation in the condenser is sensitive to the absolute temperature, this drift can alter the expected counting efficiency of the instrument. The EPROM (Erasable Programmable Read-Only Memory) chip in the TSI 3010 CPC was modified to allow $T_s$ and $T_c$ to be specified and controlled independently to 38° C. and 2° C., respectively. Thus minimizes the sensitivity of the instrument performance to the ambient (cabin) temperature. The counting efficiency was measured by comparison of calibration aerosols of salt and agglomerated silver with an electrometer standard for particles as small as 4.5 nm.

The above modifications in the TSI 3010 CPC produce an ultra fine CNC that is used in the preferred embodiment 100. This ultra fine CNC combines the condensation efficiency of ultra fine particles in the Stolzenburg and McMurry (1989) design with the higher flow rates of conventional clean-room type CNCs. As a result, counting rates are sufficiently large to provide adequate signal-to-noise ratios even at low number concentrations. In particular, the counting efficiency for ultra fine particles is improved by increasing the difference in temperatures in the saturator and the condenser. The resulting instrument shows both high efficiency in detecting ultra fine particles and good counting statistics at low concentrations.

Figure 7:
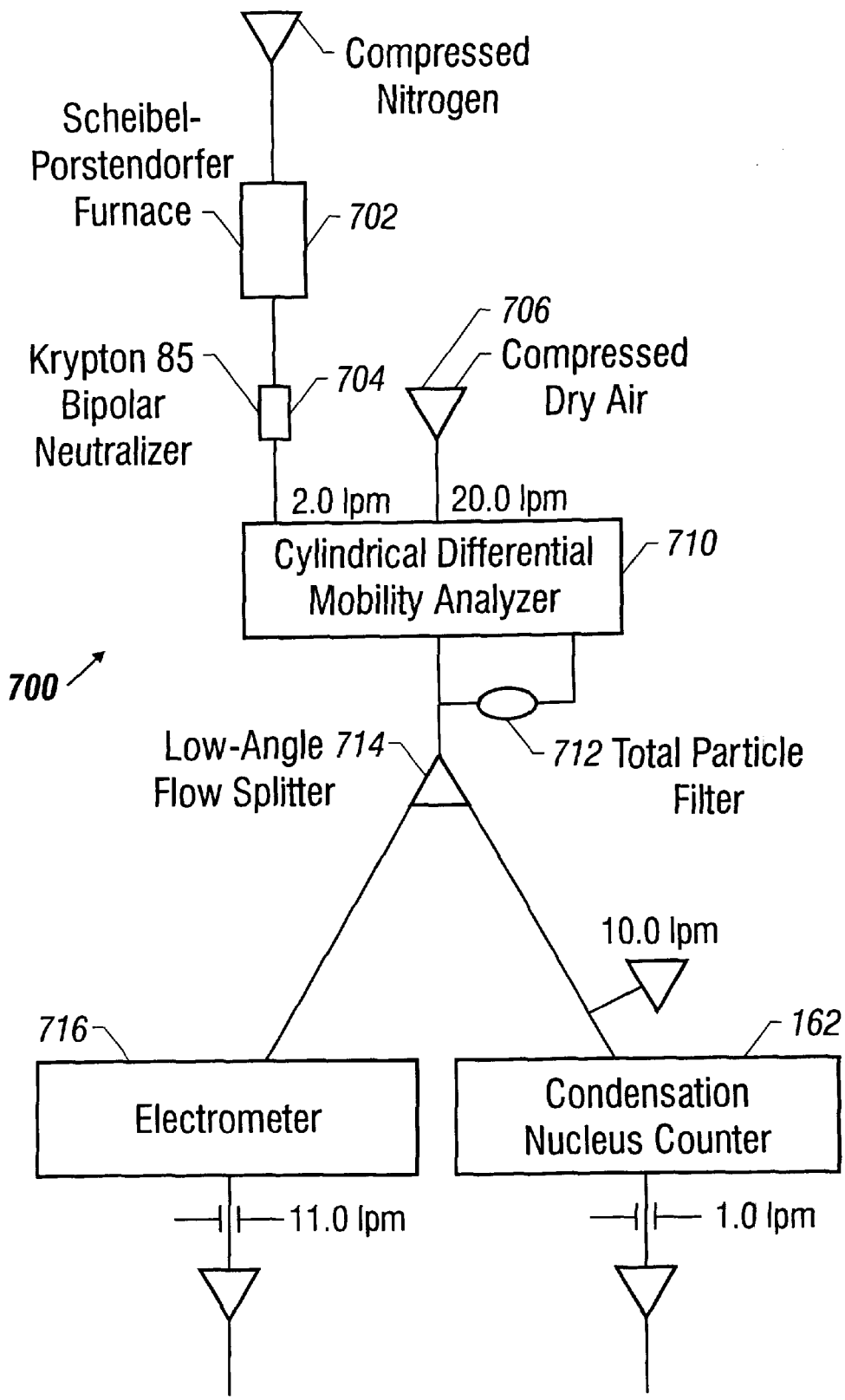
FIG. 7 shows the apparatus for calibration of the improved condensation nucleus counter that is used in the preferred embodiment of the present invention.
Figure 8:
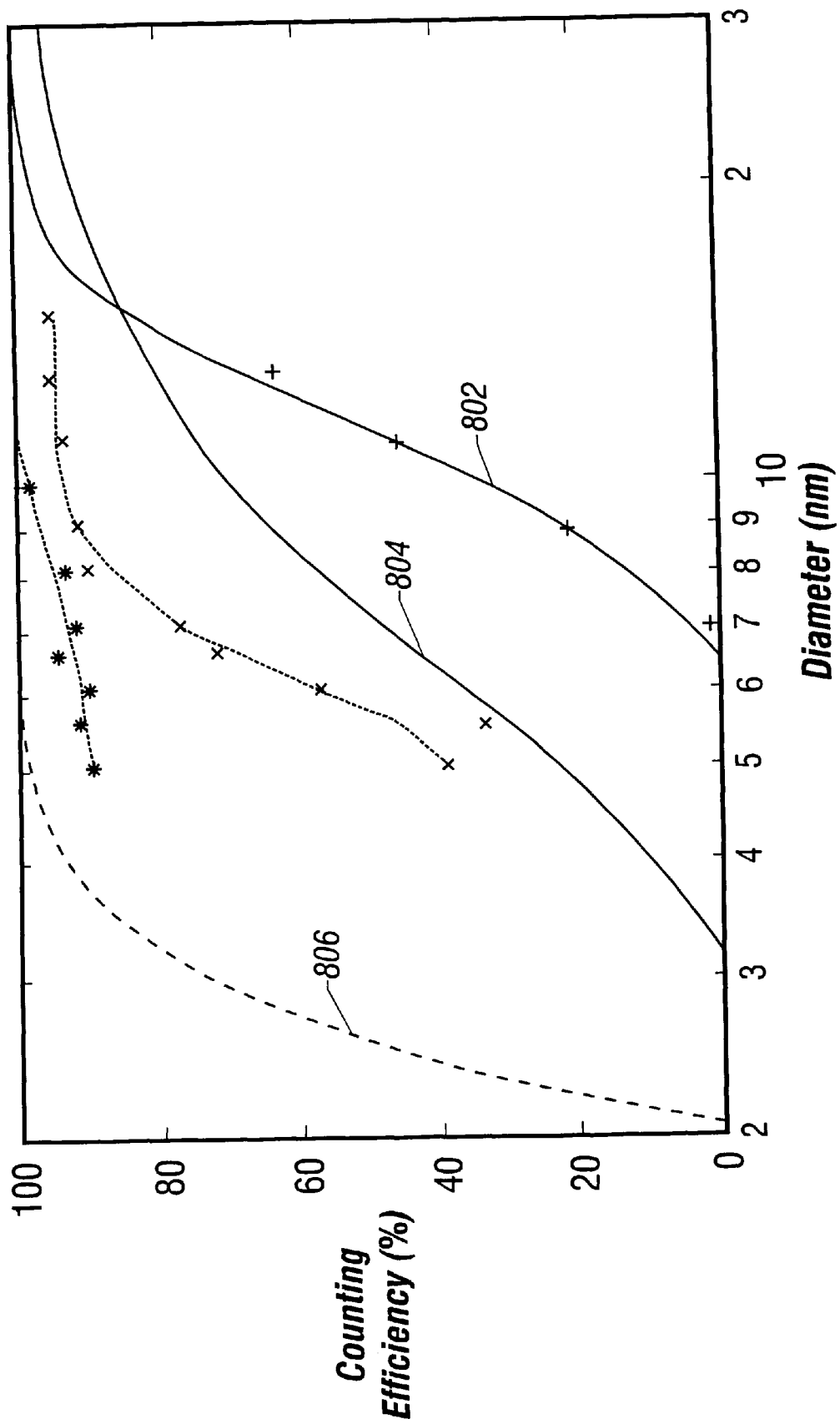
FIG. 8 shows both the calculated and measured particle counting efficiency of the condensation nucleus counter used in the present invention.

The counting efficiency of the modified particle counter was determined by comparing the modified counter's performance to a known electrometer standard (TSI, model 3068). A calibration apparatus 700 for this measurement is illustrated in FIG. 7. A vaporization/condensation source 702 generated aerosol at a flow rate of about 2 liter per minute that was classified to a known particle size in a cylindrical mobility classifier 710 (TSI, model 3071) and then diluted to a flow rate of 22 liter per minute with particle-free air by a total particle filter 712. The resulting flow was divided equally in a low-angle flow splitter 714 (TSI, model 2009) between an electrometer 716 (calibrated at 11 liter per minute) and the modified CNC 162 (pulling 1 liter per minute with 10 liter per minute bypass flow). The tubing leading to both instruments was identical up to the instrument entrances, using flexible conductive tubing to connect the flow splitter to the inlets. Hence, the number of particles counted in both cases could be compared in order to calculate the counting efficiencies. The results of these experiments are illustrated in FIG. 8 for two types of source aerosol, silver (Ag) and salt (NaCl). FIG. 8 shows the particle counting efficiency for the modified CPC, compared with several commercially available models. The data were taken with the test system 700 shown in FIG. 7. NaCl was used to generate aerosol for the DT=25° C. data indicated by crosses (x). Ag was used to generate the data for DT=17° C. indicated by pluses (+) and DT=36° C. indicated by asterisks (*), respectively. The thick line 802, the solid line 804, and the dashed line 806 represent the calibration curve of TSI3010 CPC, 3022 CPC, and 3025 CPC, respectively.

A potential limitation in improving counting efficiency by increasing DT is the possible artifact of homogeneous nucleation in the CNC leading to spurious counts in the measurements. The conditions most susceptible to allowing homogeneous nucleation include high supersaturation of condensible vapor and low preexisting aerosol surface area (Seinfeld, 1986). For DT up to 36° C., no particles were detected for a particle-free air stream. This demonstrates that for the operating temperatures of $T_s=38°$ C. and $T_c=2°$ C. spurious counts should not be detected.

Other System Components

1. Laminar Flow Element

The performance of the automated mobility classified aerosol detector is determined by the volumetric ratio of flow of the measuring aerosol and sheath gas and outgoing classified aerosol and exhaust gas. The inventors use the linear dependence of the pressure drop on the volumetric flow rate in a fully-developed laminar tube flow to measure this quantity on all four flows. A flow in a tube is laminar when the Reynolds number $$R_e = \frac{\rho v d}{\mu} \quad (10)$$

is approximately below 2000. $\rho$ is the gas density, U is the flow velocity, d is the tube diameter, and $\mu$ is the gas viscosity. The desirable length of the tube to achieve a fully-developed laminar velocity profile in the tube flow is approximately given by $$L_{FD}=d \cdot 0.05 R_e. \quad (11)$$

If the tube length, L, is long compared to $L_{FD}$, the pressure drop across the length of the tube is linearly dependent on the flow rate Q:

$$\Delta P = \frac{64 \mu L Q}{\pi d^4}. \quad (12)$$

Laminar flow metering elements were installed on all four flows in the preferred embodiment as shown in FIG. 1 to the differential mobility analyzer 150, with electric differential pressure transducers being used to monitor the flow rates. For a small aerosol inlet and classified aerosol outlet flows, a single stainless steel tube was used as the pressure drop element. The larger sheath and exhaust aerosol flows required use of a bundle of tubes to achieve fully developed laminar flow in a compact geometry. These elements were manufactured by rolling alternating layers of corrugated stainless steel shim stack and flat shim stock around a stainless steel mandrel.

2. AMCAD Software

The inventors also developed a control software to drive each of these components synchronously and to record data therefrom. The software was written using a C-compatible development program (National Instruments, LabWindows CVI) on a notebook-style computer (e.g., a IBM Thinkpad 750). The user interface allows the user to initiate different modes of operation (automatic or manual trigger) and switch sampling ports (bag sampling or DMA-bypass), while monitoring the flow rates, temperature, pressure, humidity, valve states, and CNC performance. Digital and analog data acquisition are accomplished with a PCMCIA card with 16 single-ended analog channels and 16 digital input/output channels (National Instruments, DAQCard 700). The software coordinates the filling and sampling from the double-bag sampler 200 so that a sample is drawn immediately after a bag is filled. The voltage ramp in the RDMA 150 is started after a 5-s delay to allow new sample to reach the RDMA 150 and the flow controls to reestablish constant flow ratios after the perturbation of the valve switch. Particle counts detected by the CNC 162 during 1-s intervals are transmitted serially from the CNC 162 to the computer using the hardware-coded EPROM downloading commands in the CNC 162. A real-time display shows the raw counts recorded against the current RDMA voltage, so that the raw data illustrate general distribution characteristics on a time-shifted axis.

System Flow Control

One of the important aspects of the AMCAD system 100 in accordance with the present invention is the flow control. This affects the measurements of the DMA 150 and the CNC 162 and thereby the performance of the system 100.

Referring to FIG. 1, the flow passing through the neutralizer 122 is divided into three streams: the aerosol flow $Q_a$ and clean sheath flow $Q_c$ to the DMA 150 and the dilution flow $Q_d$ to the CNC 162. The electric field controlled by the voltage difference between the two parallel electrode disks in the DMA 150 selects particles of a narrow range of mobilities into the sample flow $Q_s$ exiting the DMA 150 at the output port 159 while the main excess flow $Q_m$ removes the remainder of the flow at the port 157.

The sample flow $Q_s$ is mixed with the dilution flow $Q_d$, which has been filtered and dried. The three-way valve 160 at the CNC inlet 161 allows direct sampling of the inlet stream by bypassing the sampler 200 and DMA 150. The CNC flow is set by a critical orifice 166 preferably at a rate of 1 liter per minute. The excess DMA flow $Q_m$ exits the main outlet 157 of the DMA 150 to a critical orifice 164. The critical orifice 164 is preferably set to have a flow rate of 5 liter per minute. At the $Q_m$ stream exiting the DMA 150, probes are installed (not shown) to monitor the temperature and relative humidity. The pressure is measured with an absolute pressure transducer (not shown). The output flows controlled by the two critical orifices 164 and 166 are pulled by a vacuum pump 170 in the downstream.

Four flow rates are monitored in the preferred system 100 of FIG. 1 by measuring the pressure drop with electronic differential pressure transducers across laminar flow elements in the lines. In the sheath flow lines $Q_c$ and $Q_m$ of a predetermined flow rate (e.g. the flow rate is set at about 5 liter per minute), the pressure drops consist of "milli-channel flow elements", consisting of more than a hundred millimeter-width parallel channels formed by corrugated stainless steel shim stock with pressure taps just upstream and downstream of the restriction. In the aerosol flow lines ($Q_a$ and $Q_s$) of a predetermined flow rate (e.g.,0.5 liter per minute), each restriction consists of a capillary tube with one pressure tap far enough downstream from the entrance to be beyond the hydrodynamic development region of the flow and a second pressure tap just before the capillary exit. The relationship of pressure drop to flow through the restrictions is linear for the flow ranges for both elements. The transducer output signals are proportional to the pressure drops.

Five plug valves 130, 132, 134, 144, and 158 in the system along with the valve 160 allow isolation of the aerosol and sheath flows so that the flow transducers can be calibrated in place with a flow meter standard installed upstream of the charger 122.

Five flows, $Q_a$, $Q_c$, $Q_s$, $Q_m$ and $Q_d$, are preferably fixed by three steady state relationships and two controlled ratios in the AMCAD system 100. Two of the relationships are set by critical orifices 164 and 166:

$$Q_m = C_1, \quad (13)$$

$$Q_s + Q_d = C_2, \quad (14)$$

where $C_1$ and $C_2$ are two constants. For the components used in the preferred embodiment as in FIG. 1, $C_1$ and $C_2$ are preferably 5.0 liter per minute and 1.0 liter per minute, respectively. The conservation of mass in the steady state for the four DMA flows provides an additional condition:

$$Q_a + Q_c = Q_s + Q_m. \quad (15)$$

Continuous monitoring of the four flows allows the flow control system to respond to variations in the sampling pressure at the sample input 102. Deviations from the setpoint in the four DMA flows are used to control two independent controllers: one maintains a constant RDMA inlet flow ratio $C_3$ and the other a constant DMA outlet flow ratio $C_4$:

$$\frac{Q_a}{Q_c} = C_3, \quad (16)$$

$$\frac{Q_s}{Q_m} = C_4. \quad (17)$$

For the components used in the preferred embodiment as in FIG. 1, both $C_3$ and $C_4$ are preferably set to be equal to each other for optimal operation, i.e., high classifying resolution of the DMA and high counting rate. The flow constants $C_3$ and $C_4$ should not be too high since the resolution of the DMA will be reduced. On the other hand, the flow constants $C_3$ and $C_4$ should not be too low since the particle flux should be maintained at a minimum level in the flow to the CNC 162 for sufficient counting rate. In the tested prototype described herein, $C_3$ and $C_4$ were 0.1 for the particular components used. Because of the linear relationships between flow and pressure drop across the restrictions, this algorithm results in a constant flow ratio within a few tenths of one percent over the limited range of operation.

It will be understood that the dilution flow line 124 can be eliminated without affecting operability and functionality of the AMCAD system in accordance with the present invention. The dilution flow line 124 is used to accommodate the specific RDMA and CPC that were used in the tested prototype system.

The operation of the DMA 150 is primarily defined by the flow equations (15), (16), and (17). Flow rate $Q_m = C_1$ further defines the operation of the DMA 150. The flow constant $C_2$ in Equation (14) is usually set to meet the desired flow rate for optimal operation of a specific CNC 161 that is used ($Q_d$ is zero if no dilution flow is used).

The system as outlined here has critical flow orifices on the outlet lines of the AMCAD system 100 to control those flows. The flows will not be precisely constant, but may vary with pressure and altitude. A more general implementation would use a flow control device on those outlet flows to maintain them truly constant as indicated by the volumetric (laminar flow pressure drop) flow metering elements. The key to the preferred embodiment of the invention in FIG. 1 is control of the flow to maintain the ratios of volumetric flow rates to the DMA 150. This added degree of control might extend the range of altitudes over which the instrument 100 could be operated.

System Characterization

The inventors have characterized the performance of the preferred AMCAD system 100 of FIG. 1 by using the dual-bag sampler 200 shown in FIG. 2. Losses in aerosol transport lines have been estimated theoretically. The DMA 150 was a RDMA described thereabove and CNC 162 was the modified CPC. Both devices were calibrated to determine the particle transmission efficiency and instrument response functions.

1. Particle Losses in Tubing and Sampling Chamber

An essential part of an aerosol sampling system is the design of the plumbing so as to minimize particle losses in the sampling train. These losses may be estimated with careful calculations. Particle losses may also occur in the RDMA 150. Particle losses expected in the tubing preceding the detector CNC 162 can be estimated from the expected diffusion of particles in known flow conditions.

The flow rate in the 1.9-cm tubing preceding the sampler 200 is driven by ram pressure, which for a typical aircraft speed of 100 m s$^{-1}$, is estimated to be 470 liter per minute. This flow has a Reynolds number of 38000 for air of density 1.2 kg m$^{-3}$ and viscosity 2.0 kg m$^{-3}$ s-$^{1}$. If f is defined to be the number concentration of particles remaining at the end of tubing of length L and diameter d for an entrance number concentration of particles and flow rate Q, then for turbulent flow conditions, the particle losses may be determined from $$\frac{\phi}{\phi_0} = \exp\left(-\frac{\pi dLk}{Q}\right). \quad (18)$$

where the mass transfer coefficient k is given by (Friedlander, 1977):

$$\frac{kd}{D} = 0.079 \, Re \, f^{1/2} S_c^{1/2}, \quad (19)$$

where Re is the Reynolds number, Sc the Schmidt number, f the friction factor for the flow conditions, and D is the diffusivity of the particles.

Figure 9:
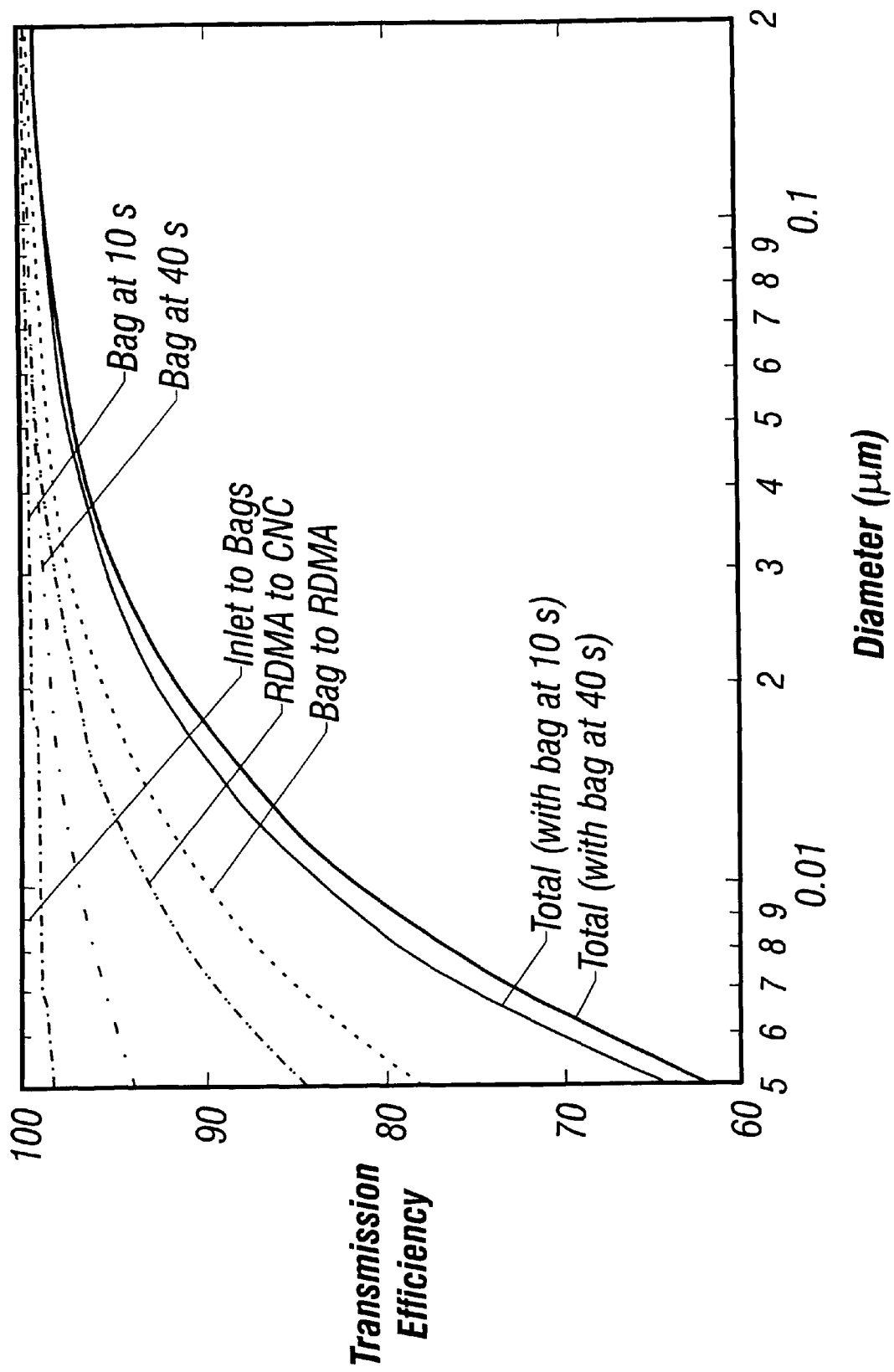
FIG. 9 shows the transmission efficiency versus particle diameter in the AMCAD plumbing system.

The air sample is held in the chamber for a duration of less than 1 minute. FIG. 9 illustrates the bounds on the particle losses in the chamber calculated based on the eddy diffusivity for the range of flow rates at which air is withdrawn from the sampler 200. The turbulent kinetic energy introduced in the sampling bag by the fill rate of the inlet of 500 liter per minute decays rapidly, such that the eddy diffusivity $k_e$ for the sample holding period can be estimated from eddies generated by the withdrawal of air from the sampling bag using the expression proposed by Okuyama et al. (1977):

$$k_e = 0.00918 Q^{3/2}. \quad (20)$$

The losses can then be calculated from the particle deposition coefficient, b, where $$\beta = \frac{\upsilon}{H} + \frac{SD}{Y\sigma} \quad (21)$$

for particles of the settling velocity U and a vessel of height H, inner surface area S, volume Y, and a diffusion boundary layer σ, which may be calculated from $k_e$ (Corner and Pendlebury, 1951; Crump and Seinfeld, 1981). Then $$\frac{\phi}{\phi_0} = \exp(-\beta t). \quad (22)$$

The bag volume shrinks continuously during sampling, beginning at a volume of 22 liters, and ending at a volume of 16 liters; the calculation is done by integrating over the sampling period.

The air withdrawn out of the sampler 200 preferably flows at 6 liter per minute, and is then split so that 0.5 liter per minute of sample air transits the RDMA 150, before it is diluted to 1 liter per minute and enters the detector CNC 162. An upper bound on the straight tube losses for these regimes of laminar flow may be estimated from the expression provided by Gormley and Kennedy (1949) for laminar flow:

$$\frac{\phi}{\phi_0} = 1 - 2.56\eta^{2/3} + 1.2\eta + 0.177\eta^{4/3}, \quad (\eta \leq 0.001) \quad (23)$$

where $$\eta = \frac{\pi DL}{Q}. \quad (24)$$

FIG. 9 illustrates the combined magnitude of each of these particle losses. These losses occur sequentially and are proportional to the particle number concentration, so that the overall losses are the product of each of these contributions, and are also illustrated in FIG. 9. Since particle diffusion losses are dependent on Brownian diffusivity, ultra fine particles will be most affected; 35% of 5 nm particles are estimated to be lost by diffusion in the tubing and the sampling bag (for a 10 s holding time) as illustrated in FIG. 9, whereas less than 1% of 200 nm particles are lost.

2. Kernel Function for AMCAD Operation

Figure 10:
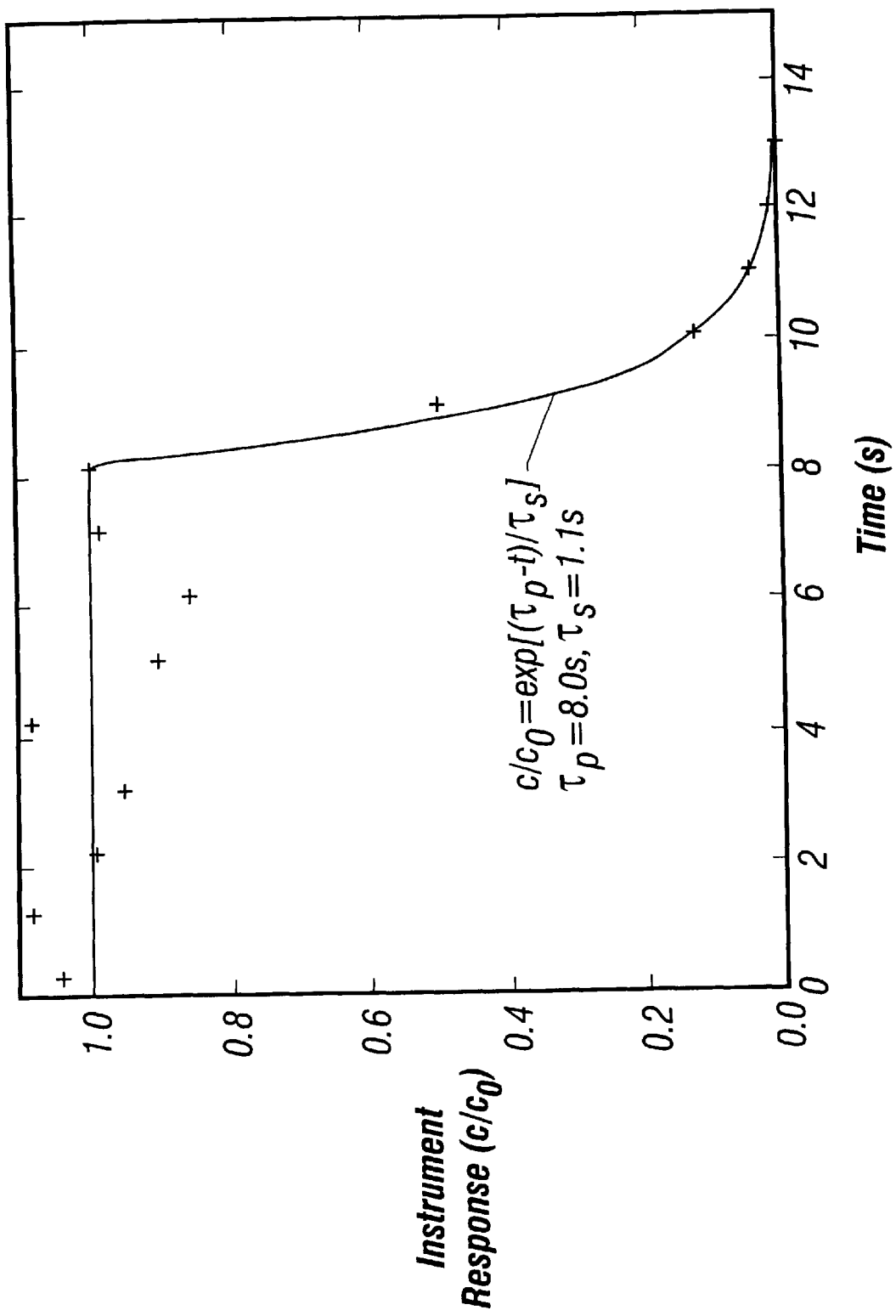
FIG. 10 shows the calculated and measured response of the radially classified aerosol detector of the present invention.

The measurement capabilities of the instrument are described by the probability that a particle of a given size will be detected, and this relationship is known as the instrument's kernel function. The kernel function for the AMCAD is defined by the following relationship for the counts recorded in the ith measurement channel $$S_i = \int_0^\infty k_i(D_p) f_i(D_p) d D_p + \epsilon_i \quad (25)$$

$$i = 1, 2, \ldots, n,$$

where f($D_p$) is the particle size distribution that is defined such that f($D_p$)d$D_p$ is the number concentration of particles with diameters between $D_p$ and $D_p$+d$D_p$, $k_i(D_p)$ is the so-called kernel function for channel i, n is the total number of measurement channels, and $\epsilon_i$ is the noise that is inherent in any experimental measurement (Russell et al., 1995). Detailed knowledge of the kernel function is a prerequisite for determination of the particle size distribution from the recorded signals. Russell et al. (1995) define the kernel function for DMA measurements of the particle size distribution in terms of experimental parameters as $$K_i(D_p) = Q_a \sum_v s(D_p, v)p(D_p, v)\phi_v(D_p)\overline{\Omega}_i[\zeta(v, D_p)], \qquad (26)$$

where $s(D_p, V)$ is the probability that the detector will count a particle of diameter $D_p$ with V charges, $\Omega_v(D_p)$ is the fraction of particles of diameter $D_p$ carrying an elementary charge of V, $p(D_p, V)$ is the probability that a particle of size $D_p$ will carry V elementary charges, $Q_a$ is the volumetric flow rate of aerosol entering the DMA, and $\overline{\Omega}_v[\zeta(V, D_p)]$ is the fraction of the particles of dimensionless mobility $\zeta(V, D_p)$ that will exit the analyzer during the counting interval of channel i. Note that the measurement procedure used here used sufficiently long delays between scans that carryover effects from previous scans can be neglected, hence we have omitted references to the scan number in the subscripts of the kernel (k) and transfer ($\Omega$) functions. For the RDMA, $$\zeta(v, D_p) = \frac{2\pi V_0}{Q_s + Q_a} \frac{r_2^2 - r_1^2}{h} \frac{veC_c}{3\pi\mu D_p}, \qquad (27)$$

where $C_c$ is the slip correction factor, e is the charge of an electron, and m is the viscosity of the carrier gas (Zhang et al., 1995). For exponential voltage scanning operation, $\overline{\Omega}_v[\zeta(V, D_p)]$ is replaced by $\overline{\Omega}_v^e[\zeta(V, D_p)]$, which can be shown to be dependent on the flow characteristics of the instrument configuration (Russell et al., 1995). The characteristic mixing time for the instrument ($\tau_s$) and the corresponding plumbing time ($\tau_p$) have been evaluated for the AMCAD's intra-instrument plumbing. The response of the CPC to a step change in concentration at the classifier was measured by recording particle counts as a function of time as the voltage at the classifier is switched from 500 to 0 volts, with the resulting concentrations plotted in FIG. 10. The best fit to the resulting residence time distribution was obtained for $\tau_p=8.0$ s and $\tau_s=1.1$ s, corresponding to the modeled flow pattern illustrated in FIG. 10 by the solid line.

A significant advance in the speed of operation of the differential mobility analyzer can be achieved when the voltage is scanned continuously rather than stepped in increments (Wang and Flagan, 1990). The operation of a DMA in scanning-mode operation at a given measurement speed differs from stepping mode operation in that the characteristic mixing time of the DMA-CNC configuration limits the speed with which the voltage can be scanned (Russell et al., 1995). This limitation of the scanning speed is, in fact, independent of the geometry of the DMA (i.e., radial vs. cylindrical), as it results entirely from the residence time of particles from the exit of the DMA to the point of detection in the CNC (which are determined by the plumbing configuration and the CNC geometry). The dependence of scan accuracy on the flow configuration between the instruments has been investigated experimentally by Flagan et al. (1993), showing that fast measurement speeds result in the asymmetric response described by Russell et al. (1995).

Figure 11A:
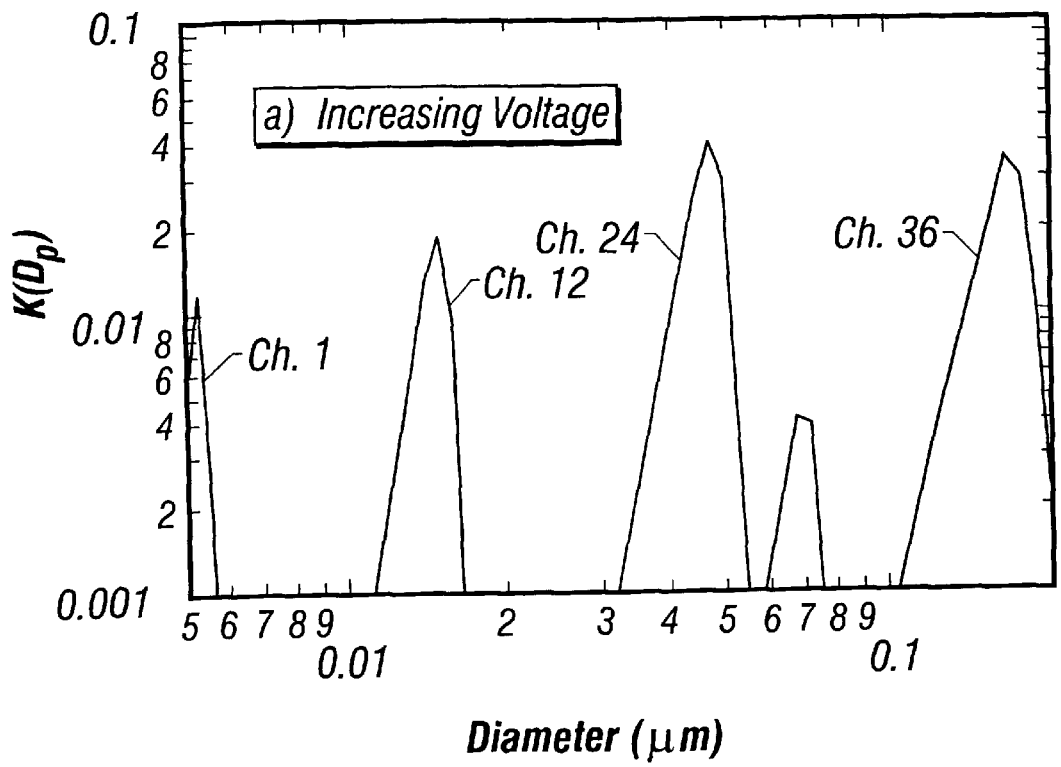
FIG. 11 shows the kernel function of the automated mobility-classified-aerosol detector in accordance with the present invention.
Figure 11B:
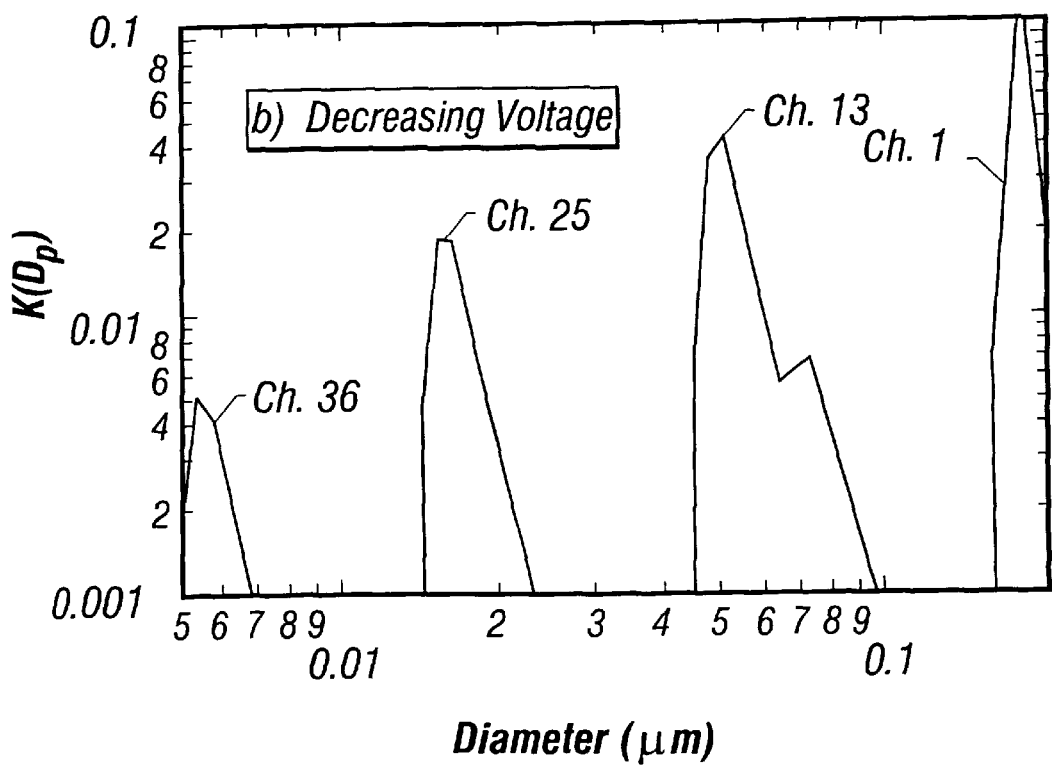

This flow pattern is then used to calculate the kernel function for each instrument channel, as illustrated by the representative channels shown in FIG. 11. Estimation of the particle size distribution requires solution of the set of Fredholm integral equation (18) for the n experimental measurements. For this purpose, the MICRON algorithm is employed to retrieve size distributions from each set of scanned measurements (Wolfenbarger and Seinfeld, 1990).

In-flight Performance

The AMCAD system 100 using the dual-bag sampler 200 described above has been mounted aboard a research aircraft operated by the University of Washington (C131a). A series of flights based out of Monterey, Calif., during June, 1994, provided an opportunity to demonstrate the performance of the AMCAD instrument in measurement of aerosol size distributions in the marine boundary layer. For this purpose, the measurement conditions in the instrument were carefully monitored. Results are presented here for in-flight variations in temperature, relative humidity, pressure and flow. Temperature and pressures monitored in the airstream are used to correct the kernel function in order to interpret the data signals, since particle mobility is a function of both air pressure and temperature.

1. Temperature and Humidity

Figure 12:
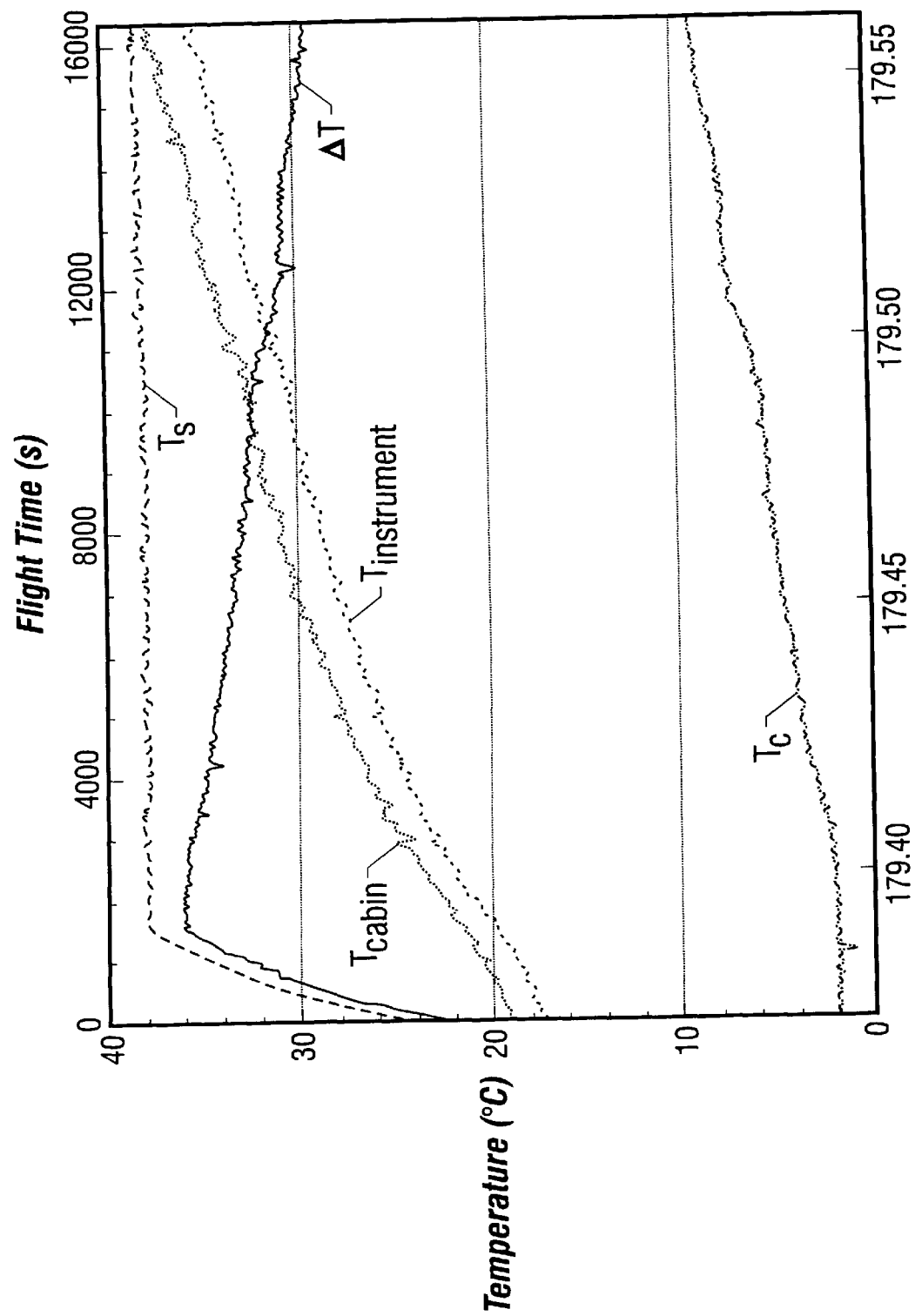
FIG. 12 illustrates the temperature variation in flight.

The air sample entering the AMCAD is heated from the ambient temperature by deceleration of the air on entering the aircraft. The resulting temperature is plotted in FIG. 12. The measurements were taken during a flight on the University of Washington C131a aircraft. The temperature of the saturator $T_s$, the temperature of the condenser $T_c$, the temperature of the aircraft cabin $T_{cabin}$, and the instrument temperature $T_{instrument}$ are shown in the FIG. 12. The instrument and cabin temperature measurements have electrically-generated noise in the signals resulting in ±3° C. In FIG. 12, these fluctuations have been removed by evaluating the mean values for each 45-second measurement period. The temperature of the air at the point of measurement in the classifier 150 tracks the cabin temperature closely, since heating of the instrument package can result in additional warming of the sampled air.

During the course of the flight, increase in the aircraft cabin temperature can preclude the CNC condenser from maintaining the temperature setpoint of 2° C. The resulting drift in the temperatures of the saturator and the condenser will alter the counting efficiency for ultra fine particles. The inventors can correct for diminished CNC performance for each size distribution by monitoring the temperatures of the saturator and condenser as illustrated in FIG. 12.

Heating of the sampled air dries the airstream, so that the humidity at which particles are measured is between 20% and 40% throughout the flight. The resulting particle sizes measured are dry nuclei diameters.

2. Pressure and Flow Rates

Figure 13:
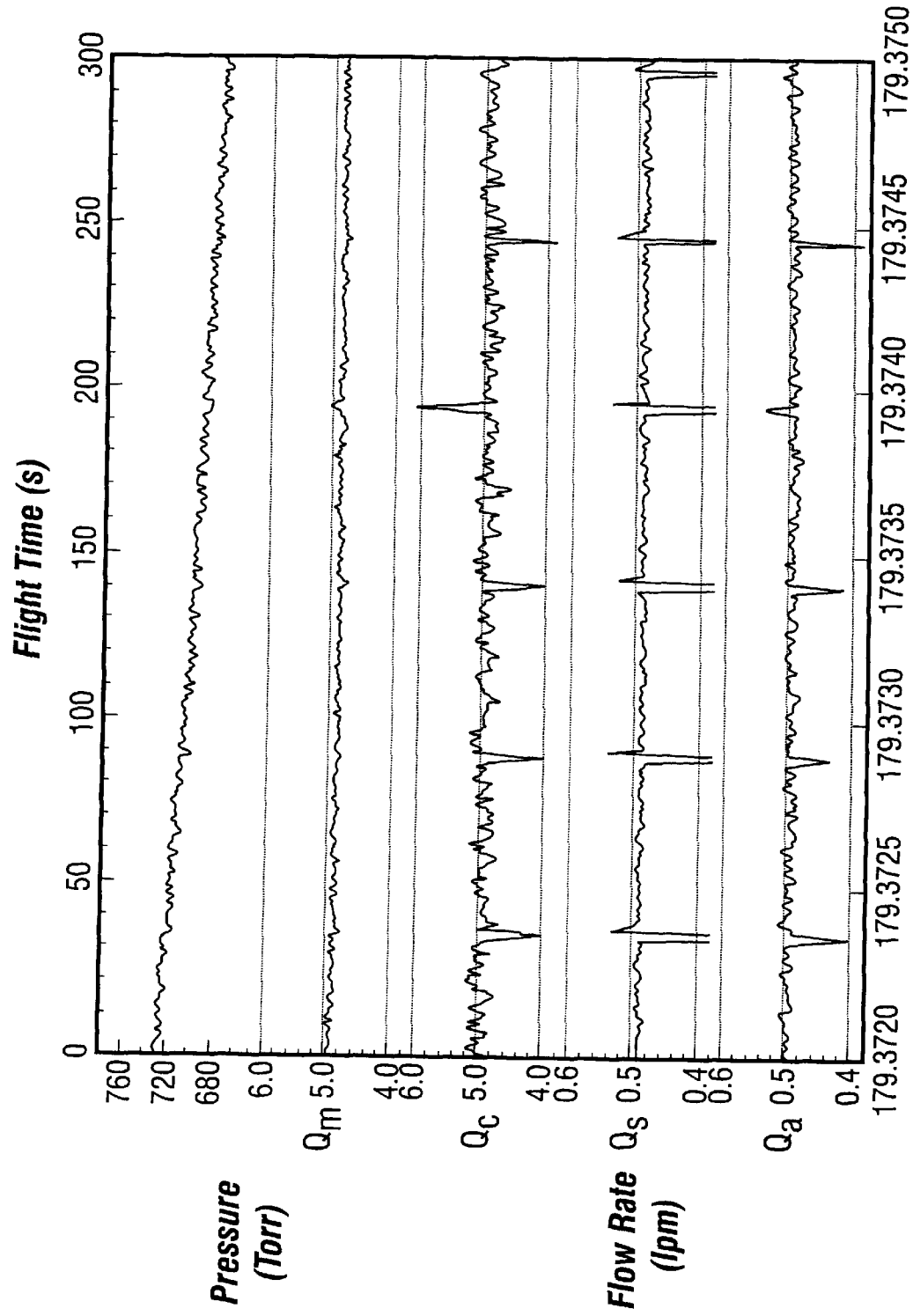
FIG. 13 shows the performance of the flow control system in a tested flight.

Air is drawn into the AMCAD of FIG. 1 from the bag sampler 200, which is in equilibrium with the aircraft's unpressurized cabin. Consequently, the pressure in the instrument varies with altitude. The feedback algorithm used in controlling the flow rates in the instrument provides constant volumetric flow rates in the instrument, so that the shape of the transfer function, and hence the size resolution of the measurement, is maintained. The effectiveness of the control algorithm is illustrated by FIG. 13, in which the flow rates are illustrated for a single flight, during both ascents and descents through the boundary layer. The high frequency fluctuations of ±6 torr in pressure result in part from electrically generated noise in the signal.

When the absolute pressure within the system changes due to ascent or descent of the aircraft, flow imbalances develop within the system. In particular, conservation of mass dictates a net inflow to or outflow from the RDMA 150 in order to effect a change in the pressure of the finite volume of air contained therein. During such changes the controllers still maintain constant inlet and outlet flow ratios, thereby maintaining the shape of the RDMA transfer function under these transient conditions.

In FIG. 13, the switch between the dual sampling bags is marked by a spike in the flow rates of ±0.5 liter per minute in $Q_c$ and ±0.3 liter per minute in $Q_a$. Switching between bags results in an interruption of the flow to the instrument, which must be compensated by the flow control. These perturbations are almost instantaneous, corresponding to the valve actuation time of much less than 1 s. From the 1-Hz frequency data illustrated in FIG. 13, the recovery time of the flow rates is estimated to be less than is, so that the flow has stabilized before data is recorded for the measurement. Electrical noise in the flow metering results in ±1% of the reported flow rates.

Changes in pressure corresponding to altitude changes of the aircraft occur at gradual rates corresponding to the climb or descent rate of the aircraft. For the time period illustrated in FIG. 13, the pressure drops 50 torr during 300 s. Adjusting the flow rate to the resulting gradual change in absolute pressure in the instrument requires fine adjustment of the flows. As shown in FIG. 13, the volumetric flow rates are maintained to their designed flow settings during sampling intervals, within the precision of the flow measurement for the time period illustrated.

Table 2 herebelow is a comparison of the tested prototype of the preferred embodiment shown in FIG. 1 using the sampler 200 with some of the prior-art systems in measuring submicron aerosol particles from aircraft. The characteristics contained in the Table 2 are based on published descriptions from Brock et al. (1989), Hudson and Clarke (1992), Hegg et al. (1993), Frick and Hoppel (1993), and the tested results of the AMCAD.

TABLE 2

| Reference | Platform | Diameter range | Instrument | Sampling time |
|---|---|---|---|---|
| Brock et al. (1989) | UW C131a | 0.010–1.0 μm | Electrostatic aerosol (TSI) | Not specified |
| Hegg et al. (1993) | UW C131a | 0.020–0.6 μm | Diffusion battery (TSI) | 4 min |
| Frick et al. (1993) | NRL Airship | 0.010–1.2 μm | DMA (TSI) | 10 min |
| Hudson et al. (1992) | NCAR Electra | 0.020–0.6 μm | DMA (NRL) | Not specified |
| This work | UW C131a | 0.005–0.2 μm | DMA (TSI) AMCAD (CIT) | 45 s |

In summary, the present invention describes a radially classified aerosol detecting system for fast characterization of fine particle size distributions in a parameter-changing environment such as changing pressure and temperature in the in-flight measurements. Use of an alternating dual-bag sampler, an enhanced RDMA and a high-resolution CNC in combination with the implementation of flow control and feed back control of flow rates allow the preferred embodiment of the present invention to achieve high-resolution and high precision measurements under changing pressures.

Although the present invention has been described in detail with reference to a particular embodiment, one ordinarily skilled in the art to which this invention pertains will appreciate that various modifications and enhancements may be made without departing from the spirit and scope of the invention. For example, the clean sheath flow $Q_c$ of the flow line 128 of FIG. 1 can be originated from the upstream of the charger 122. The sampler 200 can have only one sampling bag or more than two sampling bags such as three dependent on the specific applications. These modifications and others are intended to be encompassed by the following claims.

What is claimed is:

1. A method of measuring aerosol particle distribution, comprising:
    providing an aerosol charging device, a differential mobility analyzer, a particle counting device, and flow conduits therebetween;
    obtaining an aerosol flow having aerosol particles;
    charging said aerosol flow by using said aerosol charging device;
    dividing said aerosol flow from said aerosol charging device into a first flow and a second flow, minimizing said aerosol particles in said second flow, and directing said first flow to said differential mobility analyzer as a sample flow and said second flow thereto as a clean air flow;
    controlling said first flow and said second flow so as to maintain a first flow rate ratio therebetween at a first predetermined value;
    partitioning said particles in said sample flow into various packets with respect to particle dimension with said differential mobility analyzer, said differential mobility analyzer exporting a classified sample flow and a main flow;
    controlling said classified sample flow and said main flow so as to maintain a second flow rate ratio therebetween at a second predetermined value;
    maintaining said main flow from said differential mobility analyzer at a first fixed flow rate; and
    measuring a number of particles in each of said various packets with respect to particle dimension to obtain said aerosol particle distribution.

2. A method as in claim 1, further comprising guiding said classified sample flow to said particle counting device and maintaining a flow rate thereof at a second fixed value.

3. A method as in claim 1, further including:
    providing a sampling device having two sampling bags; and
    achieving a continuous sampling by alternatively capturing said aerosol particles from said aerosol flow with said two sampling bags.

4. A method as in claim 1, further comprising:
    providing a voltage source, operating to supply a time-dependent ramp signal to said differential mobility analyzer.

5. A method as in claim 4, wherein said voltage source comprises an analog circuit including:
    an electronic integrator having a voltage input and an output, operating to generate a time-dependent ramp signal to an output of said voltage source;
    an integrator-controlling circuit having an output, a first input and a second input, said integrator-controlling circuit being disposed so that said output thereof is electrically connected to said voltage input of said integrator; and
    an electronic control circuit, electrically connecting to said integrator-controlling circuit, operating to affect operation of said integrator-controlling circuit.

6. A method as in claim 5, further comprising:
    making said integrator-controlling circuit to function as a voltage follower with a first operation mode of said electronic control circuit;
    making said integrator-controlling circuit to function as a voltage inverter with a second operation mode of said electronic control circuit;
    making said time dependent ramp signal continuously vary with time in an exponential fashion.

* * * * *

UNITED STATES PATENT AND TRADEMARK OFFICE
CERTIFICATE OF CORRECTION

Page 1 of 1

PATENT NO. : 5,922,976
DATED : July 13, 1999
INVENTOR(S) : Richard C. Flagan, Shouhua Zhang and Lynn M. Russell It is certified that error appears in the above-identified patent and that said Letters Patent is hereby corrected as shown below:

Column 1,
After Line 7, insert

-- Origin of the Invention

The U.S. Government has certain rights in this invention pursuant to Grant Nos. N00014-93-1-0872 and N00014-94-1-0663 awarded by the U.S. Navy. --

Signed and Sealed this

Twenty-fourth Day of July, 2001

Attest:

NICHOLAS P. GODICI
Attesting Officer
Acting Director of the United States Patent and Trademark Office